(12) United States Patent
Kerbage et al.

(10) Patent No.: US 12,233,278 B2
(45) Date of Patent: *Feb. 25, 2025

(54) LASER SYSTEM FOR ENHANCING REMINERALIZATION AND STRENGTH OF HARD TISSUE

(71) Applicant: Convergent Dental, Inc., Waltham, MA (US)

(72) Inventors: Charles Kerbage, Arlington, MA (US); Ali Badreddine, Boston, MA (US); Stephen Couitt, Auburndale, MA (US); Roni Cantor-Balan, Natick, MA (US)

(73) Assignee: Convergent Dental, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/413,943

(22) Filed: Jan. 16, 2024

(65) Prior Publication Data

US 2024/0226597 A1    Jul. 11, 2024

Related U.S. Application Data

(63) Continuation of application No. 17/139,208, filed on Dec. 31, 2020, now Pat. No. 11,918,824.
(Continued)

(51) Int. Cl.
| | | |
|---|---|---|
| *A61N 5/06* | (2006.01) | |
| *A61C 19/06* | (2006.01) | |
| *A61N 5/067* | (2006.01) | |

(52) U.S. Cl.
CPC .......... *A61N 5/0603* (2013.01); *A61C 19/063* (2013.01); *A61N 2005/0606* (2013.01); *A61N 5/067* (2021.08)

(58) Field of Classification Search
CPC ....... A61C 19/06; A61C 19/063; A61C 1/087; A61C 1/0046; A61N 5/0603; A61N 5/067; A61N 2005/0606
See application file for complete search history.

(56) References Cited

U.S. PATENT DOCUMENTS

| | | |
|---|---|---|
| 4,877,401 A | 10/1989 | Higuchi et al. |
| 5,374,266 A | 12/1994 | Kataoka et al. |
| (Continued) | | |

FOREIGN PATENT DOCUMENTS

| | | |
|---|---|---|
| CA | 2867703 A1 | 9/2013 |
| EP | 2030591 | 3/2009 |
| (Continued) | | |

OTHER PUBLICATIONS

Correa-Afonso et al, "Influence of Laser Irradiation on Pits and Fissures: An In Situ Study" <https://www.ncbi.nlm.nih.gov/pmc/articles/PMC3565555/ Feb. 2013.
(Continued)

*Primary Examiner* — Heidi M Eide
*Assistant Examiner* — Shannel Nicole Belk
(74) *Attorney, Agent, or Firm* — Goodwin Procter LLP

(57) ABSTRACT

A laser-based system and method for treatment of hard tissue enhances remineralization and fluoride uptake to improve resistance to demineralization. The system can include a laser source, an optic, and a controller for controlling the laser source and/or the optic to deliver radiation to a treatment region with desirable characteristics (e.g., to remove carbonate without damaging the tissue surface). In some cases, the system includes a handpiece having an optical element (e.g., a lens) mounted within a replaceable cartridge and adapted to modulate a laser beam to render the beam non-ablative, prior to the laser beam's delivery to the treatment region. In some embodiments, treatment with the
(Continued)

laser can be combined with a fluoride treatment for enhanced therapeutic effect.

18 Claims, 13 Drawing Sheets

Related U.S. Application Data

(60) Provisional application No. 62/956,862, filed on Jan. 3, 2020.

(56) References Cited

U.S. PATENT DOCUMENTS

| | | | |
|---|---|---|---|
| 5,388,987 | A | 2/1995 | Badoz et al. |
| 5,435,724 | A | 7/1995 | Goodman et al. |
| 6,669,685 | B1 | 12/2003 | Rizoiu et al. |
| 7,931,645 | B2 | 4/2011 | Strassl et al. |
| 8,011,923 | B2 | 9/2011 | Lukac et al. |
| 10,045,833 | B2 | 8/2018 | Monty et al. |
| 10,779,908 | B2 | 9/2020 | Dresser et al. |
| 11,918,824 | B2 * | 3/2024 | Kerbage ............. A61C 1/0046 |
| 2002/0164291 | A1 | 11/2002 | Cozean et al. |
| 2003/0170586 | A1 | 9/2003 | Cozean et al. |
| 2004/0248060 | A1 | 12/2004 | Cozean et al. |
| 2005/0255053 | A1 | 11/2005 | Cozean et al. |
| 2007/0160958 | A1 | 7/2007 | Belikov et al. |
| 2008/0280260 | A1 * | 11/2008 | Belikov ............... A46B 11/002 433/32 |
| 2011/0076645 | A1 | 3/2011 | Torres Zaragoza |
| 2011/0189628 | A1 | 8/2011 | Monty |
| 2011/0207075 | A1 | 8/2011 | Altshuler et al. |
| 2013/0059264 | A1 | 3/2013 | Monty |
| 2014/0093843 | A1 | 4/2014 | Altshuler et al. |
| 2015/0147718 | A1 | 5/2015 | Khakpour et al. |
| 2016/0135937 | A1 | 5/2016 | Jeng et al. |
| 2016/0143703 | A1 | 5/2016 | Convergent |
| 2017/0319277 | A1 | 11/2017 | Cantor-Balan et al. |
| 2018/0325622 | A1 * | 11/2018 | Groves, Jr. .......... A61C 19/066 |
| 2019/0117333 | A1 | 4/2019 | Groves, Jr. et al. |

FOREIGN PATENT DOCUMENTS

| | | |
|---|---|---|
| JP | 2004049577 A | 2/2004 |
| JP | 2009167135 A | 7/2009 |
| JP | 2016-163749 | 9/2016 |
| WO | 2003059305 A1 | 7/2003 |
| WO | 2003076015 A1 | 9/2003 |
| WO | 2012008599 | 1/2012 |
| WO | 2012105972 A1 | 8/2012 |

OTHER PUBLICATIONS

Daniel Nguyen et al., "High-speed scanning ablation of dental hard tissues with a ?= 9.3 ?m CO2 laser: adhesion, mechanical strength, heat accumulation, and peripheral thermal damage"; Journal of Biomedical Optics 16 (7), 071410 (Jul. 2011).
Lidiany Azevedo, et al, "Carbon dioxide laser in dental caries prevention ", Oct. 2004 <https://www.researchgate.net/publication/8407439 Carbon_dioxide_laser_in_dental_caries_prevention>.
Marcella Esteves-Oliveira et al, "Screening of CO2 Laser (10.6??m) Parameters for Prevention of Enamel Erosion" Photomedicine and Laser Surgery, vol. 30, Nov. 6, 2012, pp. 330-338.
Kwang K. Chang, et al. "Adhesion studies on dental enamel surfaces irradiated by a rapidly scanned carbon dioxide laser", Proc SPIE Int Soc Opt Eng. Jan. 1, 2011; 7884: doi:10,1117/12.878892.
Kenneth H. Chan, et al., "Analysis of enamel surface damage after selective laser ablation of composite from tooth surfaces", Photonics Lasers Med. Feb. 1, 2014; 3(1): 37-45.
Daniel Fried, et al., "Infrared Spectroscopy Of Laser Irradiated Dental Hard Tissues Using The Advanced Light Source" Apr. 27, 2001 <http://citeseerx.ist.psu.edu/viewdoc/download?doi=10.1.1.158.7297&rep=rep1&type=pdf>.
Michael Staninec, et al., "Pulpal Effects Of Enamel Ablation With A Microsecond Pulsed ?=9.3-?m CO2 Laser" Lasers Surg Med. Apr. 2009; 41 (4): 256-263.
Shlomo Assa, et al. "Ablation Of Dental Hard Tissues With A Microsecond Pulsed Carbon Dioxide Laser Operating At 9.3-?m With An Integrated Scanner" Proc SPIE Int Soc Opt Eng. 2008; 6843:684308. doi: 10.1117/12.778799.
Saba Hedayatollnajafi, et al. "Dentin Bond Strength After Ablation Using A Co2 Laser Operating At High Pulse Repetition Rates" Proc SPIE Int Soc Opt Eng. Feb. 18, 2009; 7162:71620F-.doi:1117/12.816862.
Saba Hedayatollahnajafi, et al."Relation between Acid Dissolution and Histological Alteration of Heated Tooth Enamel (with 1 color plate)" Proc SPIE Int Soc Opt Eng. Feb. 18, 7162: 71620F-.doi:10.11/12.816862.
Fowler Bo, et al., "Changes in heated and in laser-irradiated human tooth enamel and their probable effects on solubility" Calcif Tissue Int. Apr. 1986; 38(4):197-208.
Giselle rodrigues de Sant'Anna, et al. "Dental Enamel Irradiated with Infrared Diode Laser and Photo-Absorbing Cream: Part 2-EDX Study" Photomed Laser Surg. Oct. 2009; 27(5): 771-782.
Kenneth H. Chan, et al., "Rapid and Selective Removal of Composite From Tooth Surfaces With a 9.3 ?m CO2 Laser Using Spectral Feedback" Lasers Surg Med. Sep. 2011; 43(8): 824-832.
Kenneth H. Chan, et al. "Selective Removal of Demineralization Using Near Infrared Cross Polarization Reflectance and a Carbon Dioxide Laser".
Leon C. Chung, et al, "Image-guided removal of occlusal caries lesions with a ?= 9.3-µm CO2 laser using near-IR transillumination" Proc SPIE Int Soc Opt. Eng. Feb. 24, 2015; 9306.
Saman K. Manesh, et al, "Nondestructive assessment of dentin demineralization using polarization sensitive optical coherence tomography after exposure to fluoride and laser irradiation" J. Biomed Mater Res B. Appl Biomater. Aug. 2009 ; 90(2): 802-812.
Peter Rechmann, et al., :"Caries inhibition in vital teeth using 9.6-?m CO2-laser irradiation" Journal of Biomedical Optics 16 (7), 071405 (Jul. 2011).
JD Featherstone, et al., "CO2 laser inhibitor of artificial caries-like lesion progression in dental enamel" J Dent Res. Jun. 1998;77(6):1397-403.
S.M. McCormack, et. al., "Scanning Electron Microscope Observations Of Co2 Laser Effects On Dental Enamel" J Dent Res 74(10): 1702-1708, Oct. 1995.
M. Hossain, et al. "Effect of Pulsed Nd:YAG Laser Irradiation on Acid Demineralization of Enamel and Dentin" J Clin Laser Med Surg. Apr. 2001;19(2):105-8.
D. Fried, et al., "Dissolution Studies Of Bovine Dental Enamel Surfaces Modified By High-Speed Scanning Ablation With A Lambda = 9.3-Microm TEA CO(2) Laser" Lasers Surg Med. Oct. 2006;38(9):837-45.
S. Tagomori, et al., "Ultrastructural Change of Enamel Exposed to a Normal Pulsed IMd-YAG Laser" Caries Res 1995;29:513-520.
Byung J. Nahm, et al. "Investigation of Acid-Etched CO2 Laser Ablated Enamel Surfaces Using Polarization Sensitive Optical Coherence Tomography" Proc SPIE Int Soc Opt Eng. Feb. 9, 2012; 8208.
Kenneth H. Chan, et al., "Selective Removal of Dental Composite using a Rapidly Scanned Carbon Dioxide Laser" Proc SPIE Int Soc Opt Eng. 2011 ; 7884.
Mozammal Hossain, et al., "Acquired Acid Resistance of Dental Hard Tissues by CO2 Laser Irradiation" Journal of Clinical Laser Medicine & Surgery </journal/pho.1>vol. 17, No. 5 | <https://www.liebertpub.com/toc/pho.1/17/5>.
J.H. Meurman, et al., "Transformation of Hydroxyapatite to Fluorapatite by Irradiation with High-Energy CO2 Laser" Caries Res 1997;31:397-400.
Daniel Fried, et al., "Multiple-Pulse Irradiation Of Dental Hard Tissues At Co2 Laser Wavelengths" Proc. SPIE 2394, Lasers in Dentistry, (May 1, 1995).

(56) References Cited

OTHER PUBLICATIONS

Daniel Fried, et al., "Thermal And Chemical Modification Of Dentin Ba Pulsed Co2 Laser Irradiation At 9 To 11 Um" Proc. SPIE 2973, Lasers in Dentistry III, (May 15, 1997).

Pinabel Viraparia, et. al., "CO2 Laser: Evidence Based Applications In Dentistry" CO2 Laser—Optimisation and Application, Dr. Dan C. Dumitras (Ed.), ISBN: 978-953-51-0351-6, InTech, Available from: http://www.intechopen.com/books/co2-laser-optimisation-and-application/co2-laserevidence- based-applications-in-dentistry.

Linn H. Maung, et al. "Near-Ir Imaging Of Thermal Changes In Enamel During Laser Ablation" Proc SPIE Int Soc Opt Eng. Mar. 5, 2010; 7546(1).

JD Featherstone, "Lasers In Dentistry 3. The Use Of Lasers For The Prevention Of Dental Caries" Ned Tijdschr Tandheelkd. May 2002;109(5):162-7.

JD Featherstone, et al., "Rational Choice Of Laser Conditions For Inhibition Of Caries Progression" Proc. SPIE 2394, Lasers in Dentistry, (May 1, 1995).

Joyce Y. Cheng, et al., "Use Of A Compact Fiber Optic Spectrometer For Spectral Feedback During The Laser Ablation Of Dental Hard Tissues And Restorative Materials" . SPIE 6137, Lasers in Dentistry XII, 61370F (Feb. 13, 2006).

JD Featherstone, et al. "Mechanism Of Laser-Induced Solubility Reduction Of Dental Enamel" Proc. SPIE 2973, Lasers in Dentistry III, (May 15, 1997).

Michael J. Zuerlein, et al. "Modeling thermal emission in dental enamel induced by 9-11 ?m laser light" Applied Surface Science 127:863-868 • May 1998.

JD Featherstone, et al., "Effect Of Pulse Duration And Repetition Rate On Co2 Laser Inhibition Of Caries Progression" Proc. SPIE 2672, Lasers in Dentistry II, (Apr. 23, 1996).

JD Featherstone, et al., "Surface Dissolution Kinetics Of Dental Hard Tissue Irradiated Over A Fluence Range Of 1 To 8 J/Cm2" Proc. SPIE 3248, Lasers in Dentistry IV, (Apr. 22, 1998).

Daniel Fried, et al., "Thermal response of hard dental tissues to 9? through 11??m CO2?laser irradiation" Optical Engineering 35(7), (Jul. 1, 1996). <https://doi.org/10.1117/1.600774>.

International Search Reporting and Written Opinion issued for PCT/US2018/032022, mailed Sep. 18, 2018.

Ertl, et al., "Hard Tissue Ablation With Pulsed CO2 Lasers", SPIE vol. 1800 pp. 176-181 (.

Gerold K.H. Eyrich, "Laser-osteotomy induced changes in bone", Medical Laser Application 20 (2005) 25-36.

M. Frentzen, et al., "Osteotomy with 80ms CO2 laser pulses—histological results", Lasers Med Sci (2003)18:119-124.

Werner, et al., "CO2 laser free-form processing of hard tissue", Therapeutic Laser Applications and Laser-Tissue Interactions III, Feb. 24, 2010 vol. 6632 663202-1-663202-6.

Ivanenko, et al., Ablation of hard bone tissue with puled CO2 Lasers, Medical Laser Application 20 (2005) 13-23.

G. D. Rajitha Gunaratne, Riaz Khan, Daniel Fick, Brett Robertson, Narendra Dahotre & Charlie Ironside (2016): A review of the physiological and histological effects of laser osteotomy, Journal of Medical Engineering & Technology, DOI: 10.1080/03091902.2016.1199743 (published online Jun. 27, 2016).

Ivanenko, et al., "Hard tissue ablation with sub-ms CO2 laser pulses with the use of air-water spray", Optical Biopsy and Tissue Optics, Proceedings of SPIE vol. 4161 (2000).

Ivanenko, et al., "In Vivo animal trials with a scanning CO2 laser Osteotome," Lasers in Surgery and Medicine 37:144-148 (2005).

Ivanenko, et al., "System development and clinical studies with a scanning CO2 laser osteotome," Optical Interactions with Tissue and Cells XVII, Proc. of SPIE vol. 6084, 60840H, (2006) 1605-7422.

Kahrs, et al., "Planning and simulation of microsugrical laser bone ablation," Int J CARS (2010) 5:155-162 (DOI 10.1007/s11548-009-0303-4).

Kuttenberger, et al., "Bone healing of the sheep tibia shaft after carbon dioxide laser osteotomy; histological results," Lasers Med Sci (2010) 25:239-249 (DOI 10.1007/s10103-009-0714-z).

Nair, et al., "Observations on pulpal response to carbon dioxide laser drilling of dentine in healthy human third molars," Lasers in Medical Science (2005) 19: 240-247 (DOI 10.1007/s10103-004-0317-7).

Werner, et al., "CO2 laser "milling" of hard tissue" Optical Interactions with Tissue and Cells XVIII, Proc. of SPIE vol. 6435, 64350E, (2007) 1605-7422.

Zhang, et al., "Optimization of Line Cut Strategy for Bone tissue ablation using Short-pulsed CO2 laser based on thermal relaxation,".

Kuttenberger, et al., "Computer-Guided CO2-laser osteotomy of the SheepTibia: Technical prerequisites and first resultes," Photomedicine and Laser Surgery, vol. 26, No. 2, 2008, pp. 129-136 (DOI: 10.1089/pho.2007.2139).

Zhu Y, Zhang X, Chen Y, et al. A comparative study on the dissolution and solubility of hydroxylapatite and fluorapatite at 25° C. and 45° C. Chem Geol. 2009;268(1-2):89-96. doi:10.1016/j.chemgeo.2009.07.014.

Shellis RP, Barbour ME, Jones SB, Addy M. Effects of pH and acid concentration on erosive dissolution of enamel, dentine, and compressed hydroxyapatite. Eur J Oral Sci. 2010; 118(5):475-482. doi:10.1111/j.1600-0722.2010.00763.x.

Shellis RP r., Featherstone JDB, Lussi A. Understanding the Chemistry of Dental Erosion. Erosive Tooth Wear From Diagnosis to Ther. 2012;25:163-179. doi:10.1159/000359943.

Shi J, Klocke A, Zhang M, Bismayer U. Thermally-induced structural modification of dental enamel apatite: Decomposition and transformation of carbonate groups. Eur J Mineral. 2005; 17(5):769-776. doi:10.1127/0935-1221/2005/0017-0769.

Barinov SM, Rau J V., Cesaro SN, et al. Carbonate release from carbonated hydroxyapatite in the wide temperature rage. J Mater Sci Mater Med. 2006; 17(7):597-604. doi:10.1007/s10856-006-9221-y.

Featherstone JDB, Fried D. Fundamental Interactions of Lasers with Dental Hard Tissues. Med Laser Appl. 2001; 16(3):181-194. doi:http://dx.doi.org/10.1078/1615-1615-00022.

Kayano T, Ochiai S, Kiyono K, Yamamoto H, Nakajima S, Mochizuki T. [Effects of Er:YAG laser irradiation on human extracted teeth]. Kokubyo Gakkai Zasshi. 1989;56(2):381-392. http://www.ncbi.nlm.nih.gov/pubmed/2794701. Accessed Aug. 28, 2019.

Rechmann P, Fried D, Le CQ, et al. Caries inhibition in vital teeth using 9.6-?m CO2-laser irradiation. J Biomed Opt. 2011;16(7):071405. doi: 10.1117/1.3564908.

Rechmann P, Charland DA, Rechmann BMT, Le CQ, Featherstone JDB. In-vivo occlusal caries prevention by pulsed CO 2 -laser and fluoride varnish treatment—A clinical pilot study. Lasers Surg Med. 2013;45(5):302-310. doi:10.1002/lsm.22141.

González-Rodríguez A, de Dios López-González J, del Castillo J de DL, Villalba-Moreno J. Comparison of effects of diode laser and CO2 laser on human teeth and their usefulness in topical fluoridation. Lasers Med Sci. 2011;26(3):317-324. doi:10.1007/s10103-010-0784-y.

Cohen J, Featherstone JDB, Le CQ, Steinberg D, Feuerstein O. Effects of CO 2 laser irradiation on tooth enamel coated with biofilm. Lasers Surg Med. 2014;46(3):216-223. doi:10.1002/lsm.22218.

Stern RH, Vahl J, Sognnaes RF. Lased Enamel: Ultrastructural Observations of Pulsed Carbon Dioxide Laser Effects. J Dent Res. 1972;51(2):455-460. doi:10.1177/00220345720510023501.

Beeking PO, Herrmann C, Zuhrt R. [Examination of laser-treated tooth surfaces after exposure to acid]. Dtsch Stomatol. 1990;40(12):490-492. http://www.ncbi.nlm.nih.gov/pubmed/2132112. Accessed Aug. 28, 2019.

Steiner-Oliveira C, Nobre-dos-Santos M, Zero DT, Eckert G, Hara AT. Effect of a pulsed CO2 laser and fluoride on the prevention of enamel and dentine erosion. Arch Oral Biol. 2010;55(2):127-133. doi: 10.1016/j.archoralbio.2009.11.010.

Ana PA, Bachmann L, Zezell DM. Lasers effects on enamel for caries prevention. Laser Phys. 2006;16(5):865-875. doi:10.1134/S1054660X06050197.

Hossain M, Nakamura Y, Kimura Y, Yamada Y, Ito M, Matsumoto K. Caries-Preventive Effect of Er:YAG Laser Irradiation with or without Water Mist. J Clin Laser Med Surg. 2000;18(2):61-65. doi:10.1089/clm.2000.18.61.

(56) References Cited

OTHER PUBLICATIONS

Corrêa-Afonso AM, Bachmann L, De Almeida CG, Corona SAM, Borsatto Mc. FTIR and SEM analysis of CO2 laser irradiated human enamel. Arch Oral Biol. 2012;57(9):1153-1158. doi:10.1016/j.archoralbio.2012.02.004.

Zezell DM, Benetti C, Veloso MN, Castro PAA, Ana PA. FTIR spectroscopy revealing the effects of laser and ionizing radiation on biological hard tissues. J Braz Chem Soc. 2015;26(12):2571-2582. doi:10.5935/0103-5053.20150246.

Nelson DGA, Wefel JS, Jongebloed WL, Featherstone JDB. Morphology, Histology and Crystallography of Human Dental Enamel Treated with Pulsed Low-Energy Infrared Laser Radiation. Caries Res. 1987;21(5):411-426. doi:10.1159/000261047.

Featherstone JDB. The science and practice of caries prevention. J Am Dent Assoc. 2000; 131(7):887-899. doi:10.14219/jada.archive.2000.0307.

Featherstone JDB, Barrett-Vespone NA, Fried D, Kantorowitz Z, Seka W. CO2 laser inhibition of artificial caries-like lesion progression in dental enamel. J Dent Res. 1998;77(6):1397-1403. doi:10.1177/00220345980770060401.

Esteves-Oliveira M, Pasaporti C, Heussen N, Eduardo CP, Lampert F, Apel C. Rehardening of acid-softened enamel and prevention of enamel softening through CO2 laser irradiation. J Dent. 2011;39(6):414-421. doi:10.1016/j.jdent.2011.03.006.

Rechmann P, Rechmann BMT, Groves WH, et al. Caries inhibition with a CO 2 9.3??m laser: An in vitro study. Lasers Surg Med. 2016;554(February):1-9. doi:10.1002/lsm.22497.

Zuerlein M, Fried D, Featherstone JDB. Modeling the Modification Depth of carbon Dioxide Laser Treated Enamel. Lasers Surg Med. 1999;25(May):335-347.

Argenta RMO, Tabchoury CPM, Cury JA. A modified pH-cycling model to evaluate fluoride effect on enamel demineralization. Pesqui Odontol Bras. 2003;17(3):241-246. doi:10.1590/S1517-74912003000300008.

Stookey GK, Featherstone JDB, Rapozo-Hilo M, et al. The Featherstone laboratory pH cycling model: A prospective, multi-site validation exercise. Am J Dent. 2011;24(5):322-328.

Featherstone JD, ten Cate JM, Shariati M, Arends J. Comparison of artificial caries-like lesions by quantitative microradiography and microhardness profiles. Caries Res. 1983;17(5):385-391. doi:10.1159/000260692.

Bahrololoomi Z, Fotuhi Ardakani F, Sorouri M, Fotuhi Ardakani F. In Vitro Comparison of the Effects of Diode Laser and CO 2 Laser on Topical Fluoride Uptake in Primary Teeth. J Dent. 2015;12(8). www.jdt.tums.ac.ir. Accessed Jul. 24, 2018.

Tepper SA, Zehnder M, Pajarola GF, Schmidlin PR. Increased fluoride uptake and acid resistance by CO 2 laser-irradiation through topically applied fluoride on human enamel in vitro. J Dent. 2004;32(8):635-641. doi:10.1016/j.jdent.2004.06.010.

International Search Report and Written Opinion for PCT/US2020/067656 dated Apr. 21, 2021.

Rechmann, P., et al., "In vitro CO2 9.3-mm short-pulsed laser caries prevention—effects of a newly developed laser irradiation pattern", Lasers in Medical Science (2020) 35, 13 pages.

L.K.A. Rodrigues, et al., "In Situ Mineral Loss Inhibition by CO2 Laser and Fluoride", 2006, J Dent Res, 85(7): 617-621.

Rodrigues, L.K.A., et al., "In situ Mineral Loss Inhibition by CO2 Laser and Fluoride", Journal of Dental Research 85(7):617-621, 2006.

* cited by examiner

| Laser Fluence +/- Fluoride | Lased ΔZ (std) | Lased ΔS (std) | Lased (n) | Unlased ΔZ (std) | Unlased ΔS (std) | Unlased (n) | *% ΔZ Reduction | *% ΔS Reduction |
|---|---|---|---|---|---|---|---|---|
| 0.9 J/cm² | 883 (335) | 72.6 (17.9) | 9 | 1318 (335) | 125 (40.3) | 9 | 33.0 | 41.9 |
| 1.2 J/cm² | 763 (322) | 55.4 (15.4) | 15 | 1809 (498) | 107 (29.4) | 15 | 57.8 | 48.2 |
| 1.4 J/cm² | 353 (157) | 40.6 (3.6) | 5 | 2041 (248) | 113 (27.6) | 5 | 82.7 | 64.1 |
| 0.9 J/cm² + F | 344 (58) | 56.9 (15.1) | 12 | 555 (140) | 92.1 (17.8) | 11 | 38.0 | 38.2 |
| 1.2 J/cm² + F | 216 (145) | 39.1 (5.4) | 13 | 665 (150) | 93.8 (35.7) | 13 | 67.5 | 58.3 |
| 1.4 J/cm² + F | 113 (63) | 33.2 (7.3) | 7 | 572 (172) | 84.6 (23.8) | 8 | 80.2 | 60.8 |
FIG. 12A
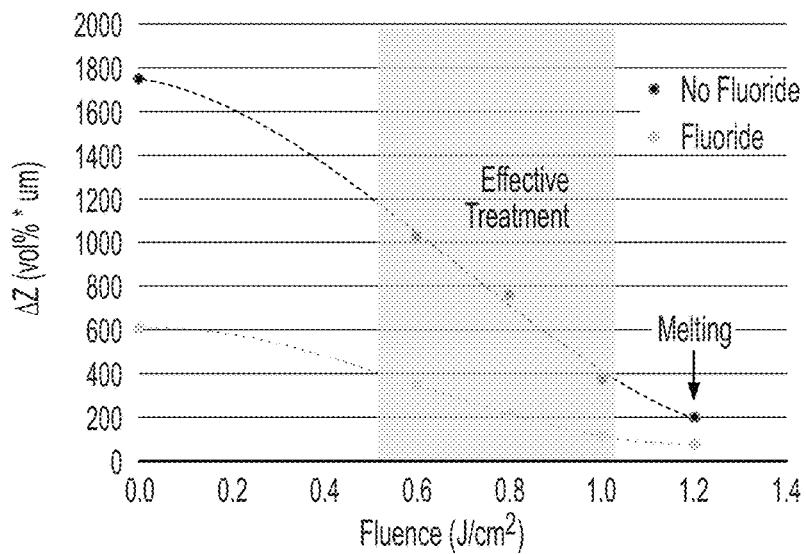
FIG. 12B
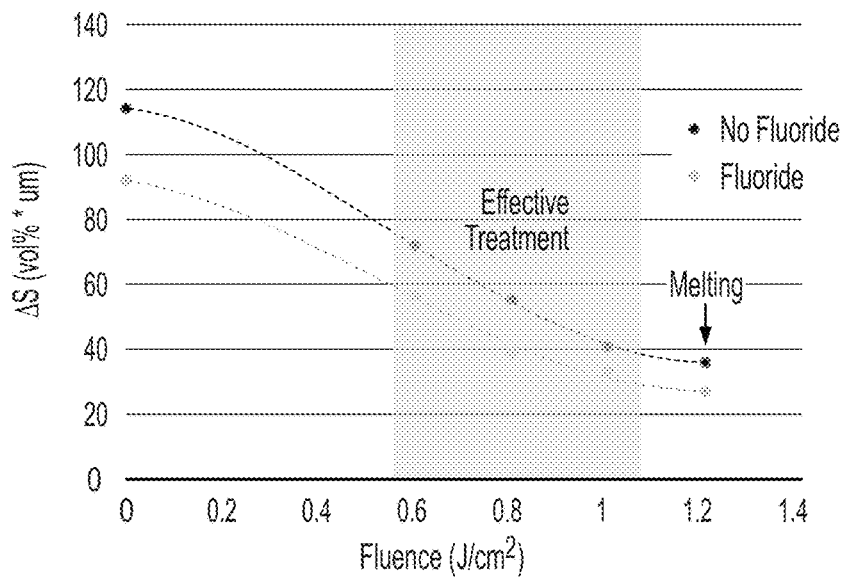
FIG. 12C

| Parameter Chart | | | | |
|---|---|---|---|---|
| Feature | Low Value | Nominal value | High Value | Unit |
| Wavelength | 9 | 9.3 | 11 | microns |
| Pulse energy | 0.1 | 6 | 50 | mJ |
| Pulse duration | 1 | 22 | 100 | μsec |
| Pule repetition rate | 0.05 | 0.75 | 10 | kHz |
| Duty cycle | 0.1 | 2.3 | 10 | % |
| Fluence per pulse | 0.01 | 0.8 | 10 | J/cm$^2$ |
| Average power | 0.1 | 4.7 | 50 | W |
| Number of locations in pattern | 1 | 217 | 1000 | |
| Point spacing | 0.1 | 0.17 | 0.5 | mm |
| Beam spot size (diameter) | 0.2 | 1 | 5 | mm |
| Total pattern time | 0.01 | 0.29 | 1 | sec |
| Total pattern size | 1 | 2.72 | 5 | mm$^2$ |
| Total treatment time (all teeth) | 5 | 10 | 15 | min |
| Treatment speed (per pattern) | 5 | 11 | 100 | mm/s |

FIG. 13

LASER SYSTEM FOR ENHANCING REMINERALIZATION AND STRENGTH OF HARD TISSUE

CROSS-REFERENCE TO RELATED APPLICATIONS

This application is a continuation of U.S. application Ser. No. 17/139,208, filed Dec. 31, 2020, which claims the benefit of priority to U.S. Provisional Patent Application No. 62/956,862 entitled "Laser System for Enhancing Remineralization and Strength of Hard Tissue," filed on Jan. 3, 2020, the contents of which are incorporated by reference herein in their entirety.

TECHNICAL FIELD

The present invention generally relates to the treatment of hard tissue using a light-emitting device (e.g., a laser source) and, more particularly, to enhancing remineralization and strength of hard tissue by directing radiation emitted by a laser source to the hard tissue.

BACKGROUND

Dental caries is a disease where tooth mineral is dissolved by acid and, if it progresses, cavities are formed. Specific bacteria in the mouth form organic acids when they feed on fermentable carbohydrates, such as sugar. These organic acids readily dissolve the carbonated hydroxyapatite mineral of tooth enamel causing mineral loss (demineralization) that initially shows up as a non-cavitated "white spot" that eventually becomes a cavity if the process continues.

The mineral that comprises about 95% by weight of tooth enamel is often described as being hydroxyapatite, which is a form of calcium phosphate. However, in actuality, tooth enamel contains numerous impurities and inclusions as a result of being formed in a biological fluid system in the human body. The mineral is better described as a carbonated hydroxyapatite in which about 1 in every 10 phosphate groups are replaced by carbonate, making the mineral manyfold more soluble in acid than pure hydroxyapatite, which has no carbonate inclusions.

Research has been performed on the use of lasers for the treatment of caries, e.g., by ablating decayed tissue so that it can be replaced with a filling material. Lasers such as Er: YAG and Nd: YAG lasers are primarily absorbed by water within the tooth rather than hydroxyapatite and may cause undesired damage to the tissue surface during a heating process. This is partly because a significant amount of the water is removed before hydroxyapatite reaches the high temperatures required for the acid-resistant effect and also from a blasting effect, as the water under the surface turns to steam. More recent research has revealed that certain $CO_2$ laser wavelengths are better absorbed in hydroxyapatite and can be effective in ablating dental tissue.

However, significantly less is known about the use of lasers to prevent caries formation and acid dissolution in the first place. Preliminary academic research has suggested that the enamel surface can be modified by heating it with short laser pulses and that such heating may lead to improved caries resistance. However, significantly more research is needed to determine the desired operating parameters for such laser treatments and to adapt the academic research to a functional system appropriate for commerical use with patients. Additionally, little is know about the effects of such laser treatments in combination with conventional caries resistance treatments, such as fluoride applications.

SUMMARY

Embodiments of the invention described herein relate to a laser treatment system that can be used to enhance both strength and reminzeralization of hard dental tissue. In some implementations, the invention includes the combined use of a laser treatment system and conventional treatment techniques such as fluoride applications, for enhanced effect. The inventors discovered that laser irradiation of dental enamel that results in the removal of carbonate from hydroxyapatite also improves the absorption of fluoride, resulting in a further modified enamel surface that approaches the composition of the less soluble form of calcium phosphate known as fluorapatite, which is even more resistant to acid attack than hydroxyapatite.

In various embodiments, the invention includes a laser source that operates in the wavelength range of 9-11 μm, such as a $CO_2$ laser. $CO_2$ lasers have several advantages over other types hard tissue lasers (e.g., Er: YAG lasers), e.g., the absorption coefficient in hydroxyapatite is about 2 factors higher. The invention can feature a handpiece for directing the 9-11 μm laser beam to a hard tissue surface in the oral cavity with desirable efficiency, minimal technique sensitivity, and a fast treatment time.

The system can be adapted to scan the laser beam using a variety of scanning techniques, e.g., using galvo-mirrors. The laser beam can be scanned across the treatment region using particular pattern(s) to allow for efficient energy delivery, producing enough localized photothermal effect to contract collagen without damaging (burning or charring) the tissue. Some such patterns are described in more detail in U.S. Patent Publication No. 2017/0319277, which is incorporated herein by reference in its entirety and attached as Appendix A.

The system may also include a laser source controller than can adjust one or more treatment parameters (e.g., laser pulse duration) according to the type of treatment selected and/or the type of tissue being treated. Various treatment parameters are described in more detail below and also in U.S. Patent Publication No. 2018/0325622, which is incorporated herein by reference in its entirety and attached as Appendix B.

In general, in one aspect, embodiments of the invention feature a system for treating a hard dental tissue. The system can include a laser source for generating a laser beam, an optic in optical communication with the laser source adapted to direct the laser beam to a treatment surface of the hard dental tissue, and a controller adapted to control the laser source and the optic to deliver the laser beam to the treatment surface to treat an area of the hard dental tissue at a rate in a range from 10 $cm^2$/min to 20 $cm^2$/min with a fluence in a range from 0.4 J/$cm^2$ up to 1.2 J/$cm^2$ to: (i) remove at least some carbonate from the treatment surface to generate an acid resistant surface without damaging the hard dental tissue, and (ii) reduce a ΔZ value of the hard dental tissue by at least 10% relative to untreated hard dental tissue.

In various embodiments, the laser source can include a $CO_2$ laser source. The laser beam can include a wavelength in a range from 9 μm to 11 μm. In some instances, the laser beam can have a spot size at the treatment surface in a range from 0.2 mm to 5 mm. The optic can include a galvanometer and/or a turning mirror. In some instances, the controller is further adapted to control the laser source to deliver the laser beam to the treatment surface in a series of pulses. In some cases, each pulse in the series of pulses include a pulse energy in a range from 0.1 mJ to 50 mJ. In some cases, each pulse in the series of pulses includes a pulse duration in a range from 1 µsec to 100 µsec. In some cases, each pulse in the series of pulses includes a repetition rate in a range from 0.05 Hz to 10 Hz. The series of pulses can include a duty cycle in a range from 0.1 to 10.

In some embodiments, the controller is adapted to deliver the series of pulses to the treatment surface in a pattern. The pattern can include a diameter in a range from 1 mm to 5 mm. The pattern can include a number of locations in a range from 1 to 1,000 (e.g., 217 locations). The spacing between each location in the pattern can be in a range from 0.1 mm to 5 mm. In some instances, the controller is also adapted to control the laser source to deliver the laser beam to the treatment surface to, when combined with a fluoride treatment, reduce a $\Delta A$ value of the dental tissue by at least 20% relative to hard dental tissue subject to the fluoride treatment. In some cases, the system can also include a fluoride delivery system adapted to deliver the fluoride treatment to the treatment surface. In some instances, the controller is further adapted to control the laser source to deliver the laser beam to the treatment surface to reduce a $\Delta S$ value of the dental tissue by at least 68% relative to untreated dental tissue. In some cases, the controller is further adapted to control the laser source to deliver the laser beam to the treatment surface to, when combined with a fluoride treatment, reduce a $\Delta S$ value of the dental tissue by at least 18% relative to hard dental tissue subject to the fluoride treatment.

In general, in another aspect, embodiments of the invention relate to a method for treating a hard dental tissue. The method can include the steps of: generating a laser beam using a laser source, directing the laser beam to a treatment surface of the hard dental tissue using an optic in optical communication with the laser source, and controlling the laser source and the optic using a controller to deliver the laser beam to the treatment surface to treat an area of the hard dental tissue at a rate in a range from 10 cm$^2$/min to 20 cm$^2$/min with a fluence in a range from 0.4 J/cm$^2$ up to 1.2 J/cm$^2$ to: (i) remove at least some carbonate from the treatment surface to generate an acid resistant surface without damaging the hard dental tissue, and (ii) reduce a $\Delta A$ value of the hard dental tissue by at least 10% relative to untreated hard dental tissue.

In various embodiments, the laser source includes a $CO_2$ laser source. The laser beam can include a wavelength in a range from 9 µm to 11 µm. In some instances, the laser beam can have a spot size at the treatment surface in a range from 0.2 mm to 5 mm. The optic can include a galvanometer and/or a turning mirror. In some instances, the controller is further adapted to control the laser source to deliver the laser beam to the treatment surface in a series of pulses. In some cases, each pulse in the series of pulses include a pulse energy in a range from 0.1 mJ to 50 mJ. In some cases, each pulse in the series of pulses includes a pulse duration in a range from 1 µsec to 100 µsec. In some cases, each pulse in the series of pulses includes a repetition rate in a range from 0.05 Hz to 10 Hz. The series of pulses can include a duty cycle in a range from 0.1 to 10.

In some embodiments, the controller is adapted to deliver the series of pulses to the treatment surface in a pattern. The pattern can include a diameter in a range from 1 mm to 5 mm. The pattern can include a number of locations in a range from 1 to 1,000 (e.g., 217 locations). The spacing between each location in the pattern can be in a range from 0.1 mm to 5 mm. In some instances, the controlling step further includes using the controller to deliver the laser beam to the treatment surface to, when combined with a fluoride treatment, reduce a $\Delta A$ value of the dental tissue by at least 20% relative to hard dental tissue subject to the fluoride treatment. In some cases, the method can further include the step of delivering the fluoride treatment to the treatment surface. In some instances, the controller is further adapted to control the laser source to deliver the laser beam to the treatment surface to reduce a $\Delta S$ value of the dental tissue by at least 68% relative to untreated dental tissue. In some cases, the controlling step further include using the controller to control the laser source to deliver the laser beam to the treatment surface to, when combined with a fluoride treatment, reduce a $\Delta S$ value of the dental tissue by at least 18% relative to hard dental tissue subject to the fluoride treatment.

BRIEF DESCRIPTION OF THE DRAWINGS

In the drawings, like reference characters generally refer to the same parts throughout the different views. In the following description, various embodiments of the present invention are described with reference to the following drawings, in which:

FIGS. 12A-C are a table and graphs showing example ΔS and ΔA measurements for various tissue surfaces subject to treatment at different fluence levels, according to various embodiments; and FIG. 13 is a chart providing example laser and treatment parameter values, according to various embodiments.

DETAILED DESCRIPTION

In various embodiments, the present invention is directed to an improved laser treatment system 100. The system 100 can reduce caries formation and acid dissolution of treated hard dental tissue when compared with conventional devices. The system 100 can include a hand piece 1 that delivers laser pulses that heat the hard tissue to remove carbonate impurities from the hydroxyapatite (and thereby enhance remineralization/decrease demineralization) without damaging the tissue. As used herein, the phrase "damaging the tissue" refers to one of burning, charring, or melting of the tissue. The removal of carbonate alone is not considered to be "damaging the tissue," under the definition used herein. Removal of carbonate without damaging the tissue is further described in U.S. Patent Publication No. 2018/0325622, which is incorporated herein by reference in its entirety and attached as Appendix B.

In various embodiments, the system 100 can also feature (i) a laser beam having a long working range (defined below), (ii) a coolant delivery system for delivering coolant (air, water, mist, etc.) to the oral treatment region and optionally (iii) a fluoride delivery system for applying fluoride to the treatment region. This application will often describe treatment of a hard dental tissue; however, in general, the inventions described herein can be adapted to be used with any suitable hard tissue (e.g., jaw, skull, and other bone regions).

In some embodiments, the laser treatment system 100 includes a $CO_2$ laser source 102 operating at a wavelength in a range of 9-11 μm (e.g., 9.3 μm) and a handpiece 1 configured to enable uniform treatment of all teeth with minimal change in technique sensitivity. The system 100 can accomplish treatment efficiently, with a fast treatment time and without need for anesthesia.

Figure 1:
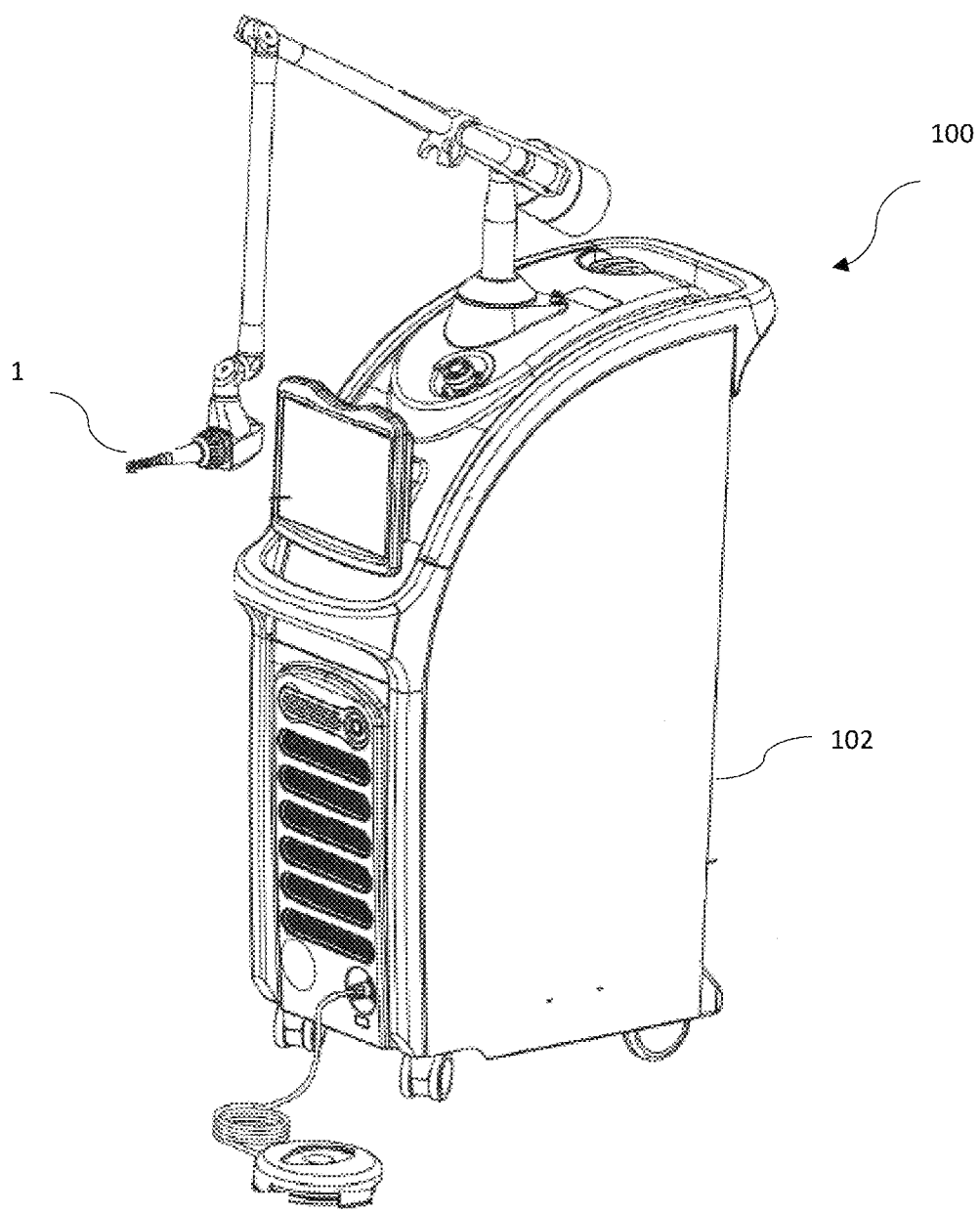
FIG. 1 is a schematic perspective view of a laser treatment system, according to various embodiments.
Figure 2:
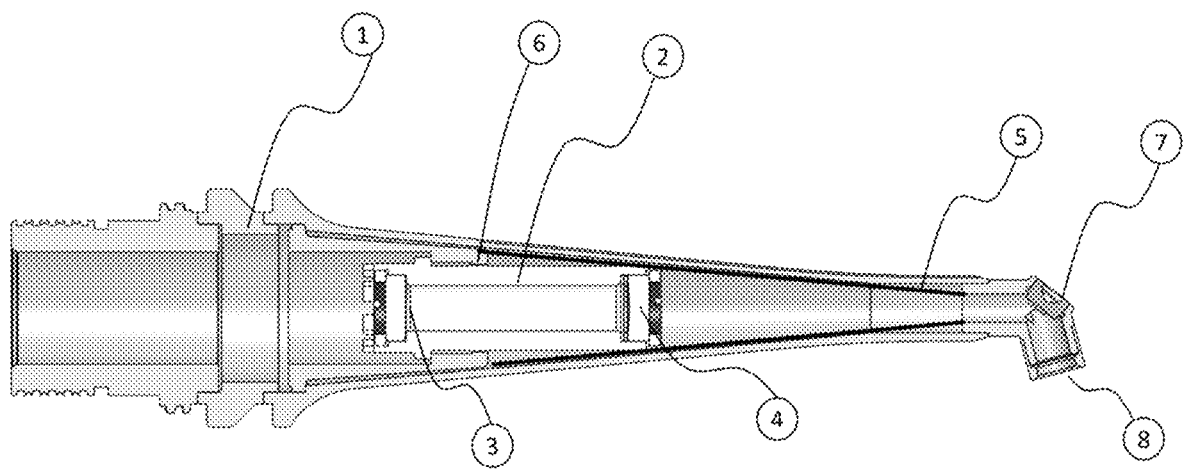
FIG. 2 is a schematic cross-sectional side view of a handpiece including an optical cartridge, according to various embodiments.

As shown in FIG. 2, the handpiece 1 may be structured and designed to receive an optical cartridge 2. The optical cartridge 2 can include at least one optical lens to modulate a laser beam passing therethrough (e.g., to generate a collimated laser beam). For example, as shown in FIG. 2, the optical cartridge can include an upstream optical lens 3 and a downstream optical lens 4. The optical cartridge 2 can be retained in the handpiece 1 using any known technique, e.g., with threading 6. The ability to replace or remove the optical cartridge 2 allows switching the laser between treatment modes, such as from an ablative mode to a non-ablative treatment mode and vice versa. In addition, the handpiece 1 can include channels or tubing 5 to deliver non-laser substances to the treatment region, e.g., cooling fluids (e.g., air, water, and mist combinations thereof) and/or a fluoride based fluid to enhance acid resistance and improve fluoride uptake. The handpiece can include an exit orifice 8 out of which the laser beam is directed, in some embodiments via a turning mirror 7. In some embodiments, the laser beam can be scanned through the hand piece and across a treatment region using galvanometers disposed upstream of the optical cartridge 2.

Figure 3:
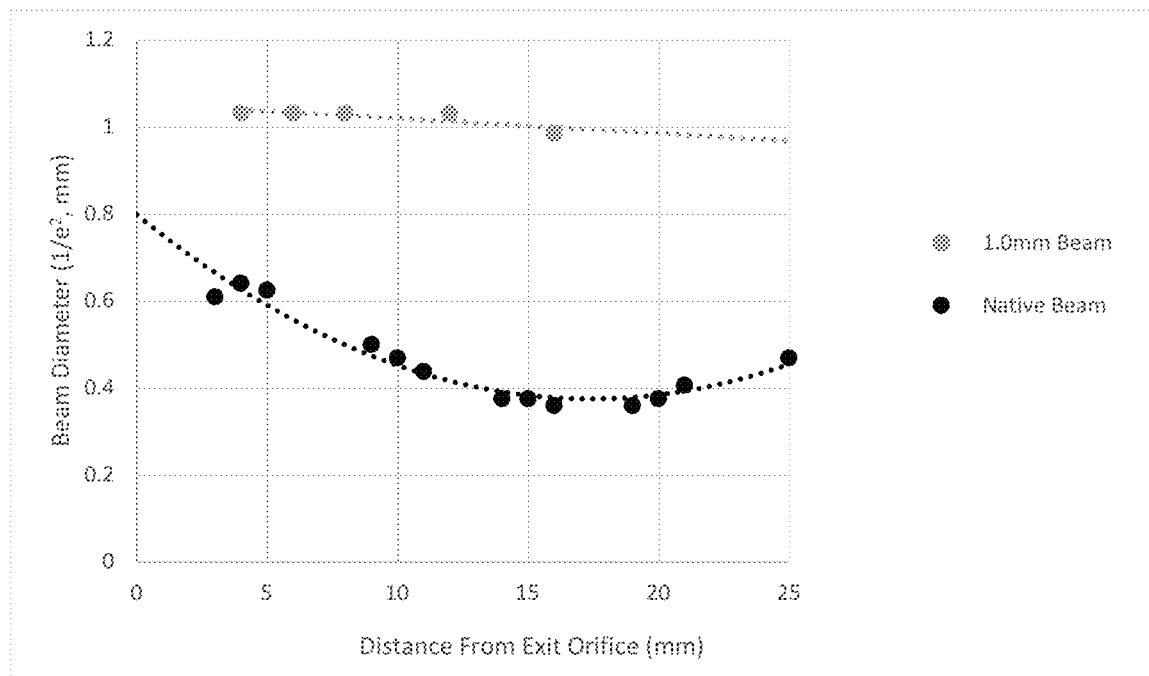
FIG. 3 is an example plot of a beam size diameter vs. distance from the handpiece exit orifice, according to various embodiments.

In some embodiments, the optical cartridge 2 can provide a laser beam having a relatively long working range. FIG. 3 is a plot of beam diameter ($1/e^2$) vs. distance from the exit orifice 8 of the handpiece 1, for a 1.0 mm beam generated with the optical cartridge 2 and for a native beam generated without the optical cartridge 2. The example data demonstrates the capability of the optical cartridge to produce a collimated and larger beam size (1 mm) than the original beam size (0.4 mm) and uniform over long working range (e.g., 5-20 mm). Because fluence is a measure of energy per unit area, generating a collimated beam and maintaining a uniform beam area (spot size) along the length of the laser beam (as opposed to a non-collimated beam that converges and diverges about a focal point) can generate a laser beam having a lower fluence which, in some instances, may result in the laser beam being non-ablative. The larger spot size can also enable for more surface area of the treatment region (e.g., a tooth) to be covered more quickly, thereby reducing treatment time.

Figure 4:
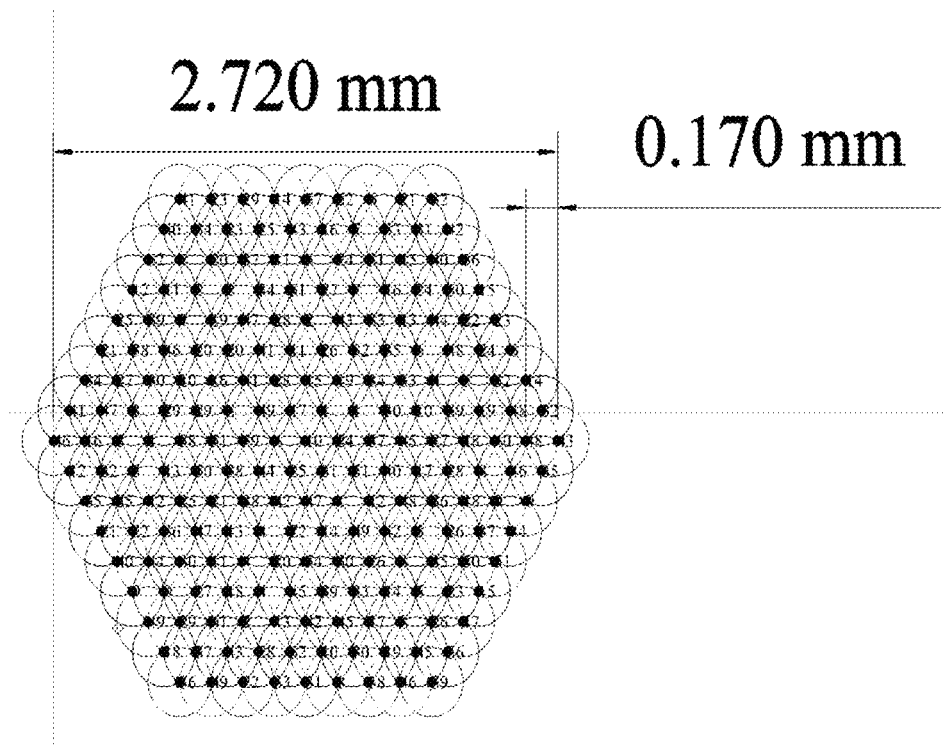
FIG. 4 is a depiction of an example treatment pattern, according to various embodiments.

In various embodiments, the laser is pulsed and scanned according to certain patterns to achieved desired levels of carbonate removal. Moreover, the laser source may be spatially scanned to provide different pulse energies at different locations as shown in FIG. 4. In various embodiments, laser and treatment parameters (e.g., as shown in FIG. 13) may be selected to optimize efficiency and to treat the tissue without damage. Example treatment patterns are described in more detail in U.S. Patent Publication No. 2017/0319277 and U.S. Patent Publication No. 2018/0325622, both of which are incorporated by reference herein in their entireties and attached as Appendices A and B.

In various embodiments, the laser treatment system 100 can operate in a manner that improves the reduction of caries formation and enhances remineralization. In particular, experiments have been conducted using the laser treatment system 100 to demonstrate this improved performance.

In a first example experiment, a 9.3 μm Solea $CO_2$ laser (Convergent Dental, Inc., Needham, MA) was used with a beam diameter of 1 mm (measured by $1/e^2$ method) that was collimated at the output of the handpiece over a range of 5 centimeters. The beam was scanned at a repetition rate of 750 Hz using a pair of controllable mirrors (galvanometers) in a pattern with a uniform spacing between centers of adjacent hits of 0.2 mm and a maximum frequency between adjacent hits of 25 Hz. This distribution of hits allowed the energy to be dissipated without accumulation of heat in the pulp. To assist in cooling, a regulated, system-delivered air flow from the handpiece was used on the samples while irradiating with the laser. Laser fluence was varied only by changing the optical pulse duration between 17-27 μs. At 17 μs, the average power is 3.5 W and fluence per pulse is 0.6 $J/cm^2$. At 27 μs, the average power is 5.7 W and fluence per pulse is 1.0 $J/cm^2$. The distance from the handpiece to the tooth samples was maintained at a set position of 10 mm to further ensure uniform delivery of energy and air to the treatment surface.

To investigate the formation and properties of an acid resistant layer, five sound human enamel samples mounted in acrylic resin and polished to 1 μm diamond grit finish (Therametrics, Inc., Indianapolis, IN) were used. The laser-treated blocks had only been exposed to thymol solution during shipment and were less than 3 months old from extraction. The Solea $CO_2$ 9.3 μm laser was used with a pulse fluence range of 0.6-1 $J/cm^2$. The blocks were serially polished up to 6 μm grit from the side to expose a cross-section of both the laser-irradiated and non-irradiated areas. The original surface that had been laser-irradiated was masked with an acid-resistant tape. The cross-section surface was exposed to 1N HCl for 1 min to erode the underlying ordinary enamel and expose the acid resistant layer, then rinsed thoroughly with water. The blocks were imaged under a 3D digital reflection microscope (Hirox RH-2000) with cross-polarization to capture the subsurface characteristics. The microscope was used to obtain 3D stacks of images over a range of depth of 50 µm.

Figures 5A, 5B:
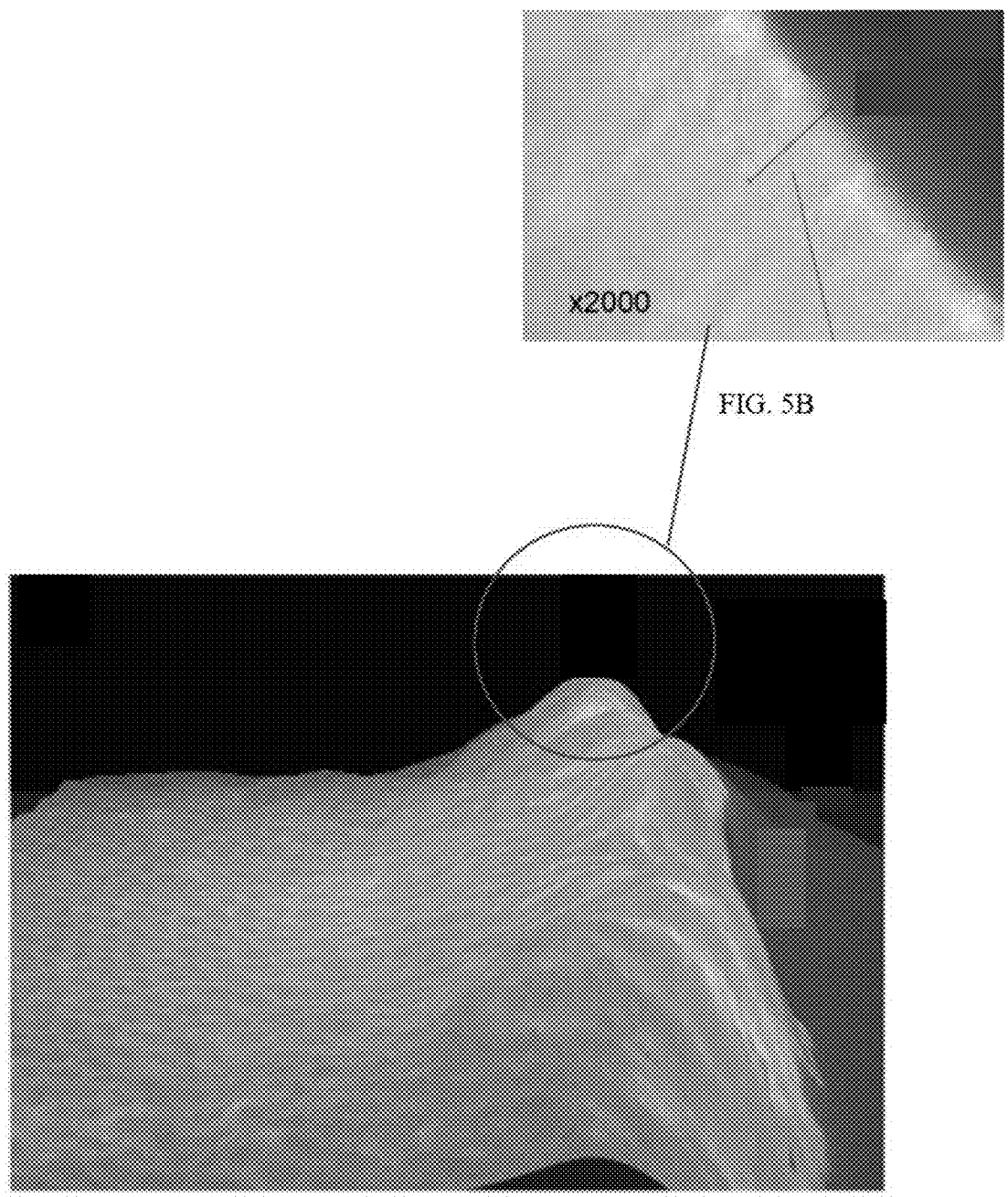
FIG. 5A depicts a lased tissue surface, according to one embodiment.
FIG. 5B depicts a magnified view of a portion of the lased tissue surface of FIG. 5A.
Figure 5D:
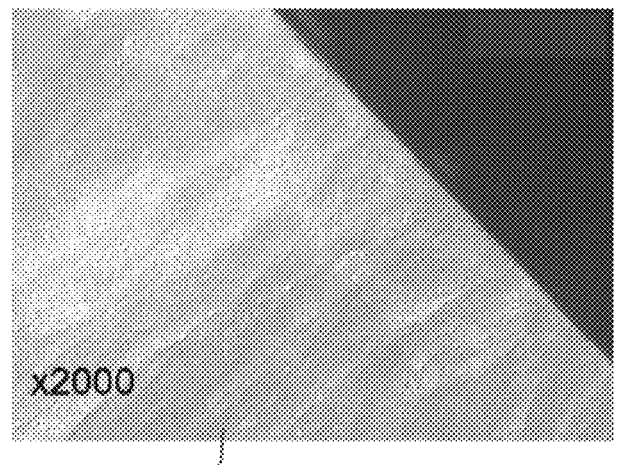
FIG. 5D depicts a magnified view of a portion of the unlased tissue surface of FIG. 5C.
Figure 5C:
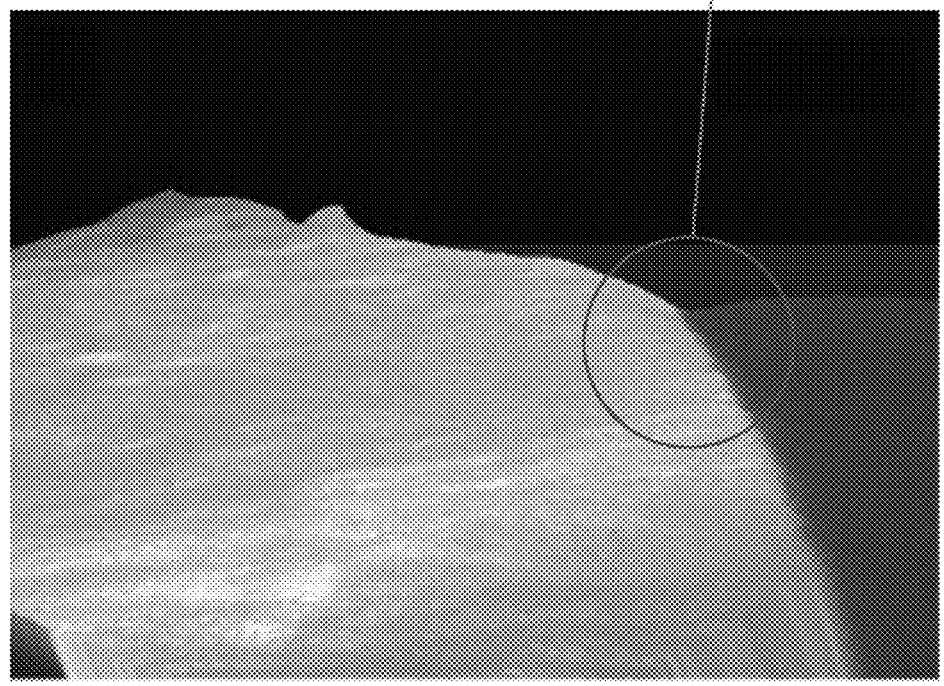
FIG. 5C depicts an unlased tissue surface, according to one embodiment.

FIG. 5B is a cross-sectioned image of enamel exposed to hydrochloric acid. In this example, an acid-resistant layer in the range of about 15 µm is created by laser-irradiation at a fluence of 0.8 J/cm2 and is exhibited as an undissolved protrusion above the underlying enamel that had experienced a rapid dissolution and is out of focus in the microscope image. FIG. 5D shows a cross section of the enamel for the non-irradiated section that dissolved uniformly with no acid-resistant layer observed. This served as a verification that the laser parameters used in the above experiment successfully formed an acid resistant layer on the enamel surface to inhibit demineralization. FIGS. 5A and 5C are 3-dimensional image stacks of the enamel samples that reveal the acid resistant layer as an unetched area near the surface for the laser irradiated sample, and a flat, evenly etched area for the non-irradiated sample.

Figure 6:
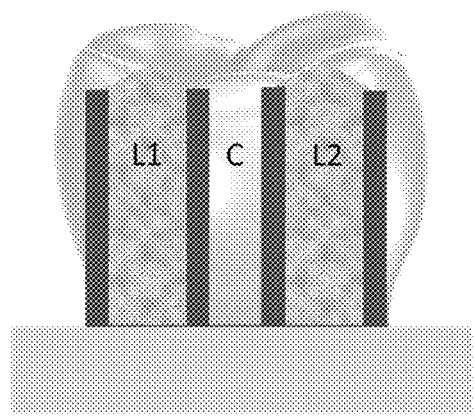
FIG. 6 depicts an experimental setup used to demonstrate performance of the laser treatment system, according to various embodiments.

In a second example experiment, to investigate reduction of caries and caries-like legions and the correlation with inhibition of surface mineral loss, seventy-four human molars with no signs of caries or fluorosis and that were less than 3 months old since extraction were obtained and stored only in thymol solution. The molars were mounted in 1" acrylic cylinders with the full crown exposed (all sides and occlusal surface) (Therametrics, Inc., Indianapolis, IN). The samples were sonicated for 5 minutes in distilled water. The samples were then air dried and split into six groups. Groups 1-3 underwent pH cycling without additional fluoride and groups 4-6 with additional fluoride. Groups 1 and 4 were laser-irradiated at a fluence of 0.6 J/cm$^2$, groups 2 and 5 at 0.8 J/cm$^2$, and groups 3 and 6 at 1.0 J/cm$^2$ on either side of the flattest area (least curvature) of the side of the crown as shown in FIG. 6. Example collected data is shown in Table 1 and Table 2 below (some loss of samples occurred due to polishing damage or other immeasurability of the sample). A non-irradiated control area was maintained in between the laser-irradiated areas. An acid-resistant, quick curing nail polish was used to mask the boundaries between laser-irradiated and non-irradiated regions along the entire height of the molar from the mounted base to the occlusal surface. FIG. 6 depicts a human molar in an acrylic resin mount. Laser-irradiated areas L1 and L2 are depicted, along with the non-irradiated control, C. The stripes are the masked regions over the full height of the exposed tooth.

TABLE 1 pH Cycling Depth Data

| Group | Additional Fluoride | Laser Fluence (J/cm$^2$) | Lased ΔZ (std) | Lased ΔZ n | Non-lased ΔZ (std) | Non-lased ΔZ n | Lased Reduction % ΔZ | p-value (95%) |
|---|---|---|---|---|---|---|---|---|
| 1 | No  | 0.6 | 1025 (253)$^a$    | 13 | 1610 (247)$^e$  | 13 | 36.3 | p = 0.001 |
| 2 | No  | 0.8 | 763 (322)$^{ab}$  | 15 | 1809 (498)$^e$  | 15 | 57.8 | p < 0.001 |
| 3 | No  | 1.0 | 374 (149)$^{bcd}$ | 5  | 1826 (325)$^e$  | 7  | 79.5 | p = 0.002 |
| 4 | Yes | 0.6 | 349 (54.1)$^{cd}$ | 12 | 591 (103)$^b$   | 12 | 40.9 | p < 0.001 |
| 5 | Yes | 0.8 | 216 (145)$^d$     | 13 | 665 (176)$^b$   | 13 | 67.5 | p < 0.001 |
| 6 | Yes | 1.0 | 113 (62.9)$^d$    | 7  | 572 (172)$^{bc}$| 8  | 80.2 | p = 0.01  |

Groups that share a lower-case letter are not significantly different.

TABLE 2 pH Cycling Surface Data

| Group | Additional Fluoride | Laser Fluence (J/cm$^2$) | Lased ΔS (std) | Lased ΔS n | Non-lased ΔS (std) | Non-lased ΔS n | Lased Reduction % ΔS | p-value (95%) |
|---|---|---|---|---|---|---|---|---|
| 1 | No  | 0.6 | 71.8 (17.1)$^{ab}$ | 10 | 124 (26.7)$^e$    | 10 | 42.1 | p = 0.002 |
| 2 | No  | 0.8 | 55.4 (15.4)$^{bc}$ | 15 | 107 (29.4)$^e$    | 15 | 48.2 | p < 0.001 |
| 3 | No  | 1.0 | 40.6 (3.6)$^{cd}$  | 5  | 113 (27.6)$^{ae}$ | 5  | 64.1 | p = 0.004 |
| 4 | Yes | 0.6 | 56.9 (15.1)$^{bc}$ | 11 | 92.1 (17.8)$^{ae}$| 11 | 38.2 | p = 0.006 |
| 5 | Yes | 0.8 | 39.1 (5.4)$^d$     | 13 | 100.1 (35.7)$^{ae}$| 13 | 60.9 | p < 0.001 |
| 6 | Yes | 1.0 | 32.5 (8.4)$^d$     | 7  | 88.2 (23.4)$^{abe}$| 7  | 63.2 | p < 0.001 |

Groups that share a lower-case letter are not significantly different.

Demineralization solution was made in the form of a 75 mM acetate buffer with 2 mM calcium and phosphate, pH balanced to 4.4 using NaOH or HCl where needed. Remineralization solution was made from 0.1 M Tris, 0.8 mM calcium and 2.4 mM phosphate, pH balanced to 7.1. A 9-pH-cycle regimen with the aforementioned solutions was followed similar to the one described in Rechmann P, Rechmann B M T, Groves W H, et al., "Caries inhibition with a $CO_2$ 9.3 µm laser: An in vitro study," *Lasers Surg Med.* 2016; 554 (February):1-9, doi:10.1002/lsm.22497, with steps of 6 hours in demineralization and 18 hours in remineralization. Approximately half the samples were exposed to a fluoride-toothpaste slurry for 1 min after each step in the cycle, using a 1:3 ratio of Crest cavity protection 1,100 ppm F toothpaste (Proctor and Gamble, Inc.) to distilled water. After 5 cycles, the solutions were replaced with fresh solutions from the same batch. After cycling, samples were stored in distilled water for no more than two weeks until the measurements were performed.

The samples were polished up to 6 at a time using an automated polisher (Metkon Forcipol 1V) with a 600 grit polishing pad until a flat cross-section in the laser-irradiated areas was reached. The samples were individually hand polished with a diamond suspension to remove polish marks for microhardness testing. The samples were serially indented (Matsuzawa Seiki DMH-2) using 25 g loads for 10 s each every 25 µm under the surface, starting at 15 µm from the outer surface until a depth of 200 µm was reached. The volume percent mineral content was calculated at each indentation position using the formula vol %=4.3 $\sqrt{KHN}$+11.3, and $\Delta Z$, a measure of depth mineral loss, was calculated as the area under the curve (with 85% as the normalized level for sound enamel), as described in Stookey G K, Featherstone J D B, Rapozo-Hilo M, et al., "The Featherstone laboratory pH cycling model: A prospective, multi-site validation exercise," *Am J Dent.* 2011; 24(5):322-328.

Figure 7:
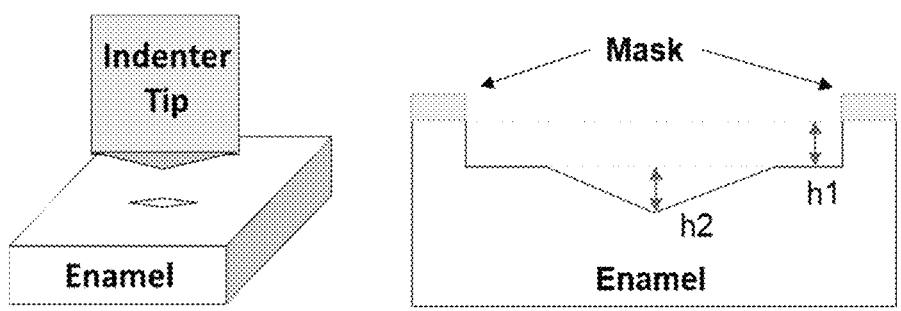
FIG. 7 depicts another experimental setup used to demonstrate performance of the laser treatment system, according to various embodiments.
Figure 8A:
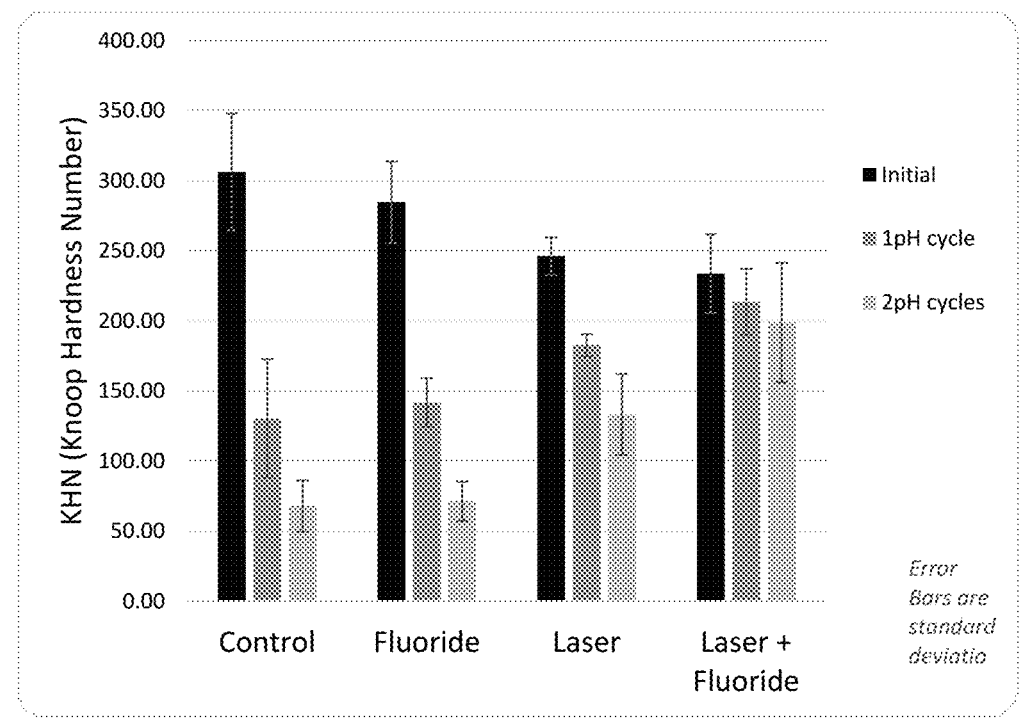
FIG. 8A is an example chart showing knoop hardness number measurements of various tissue surfaces subject to different pH cycle tests, according to various embodiments.
Figure 8B:
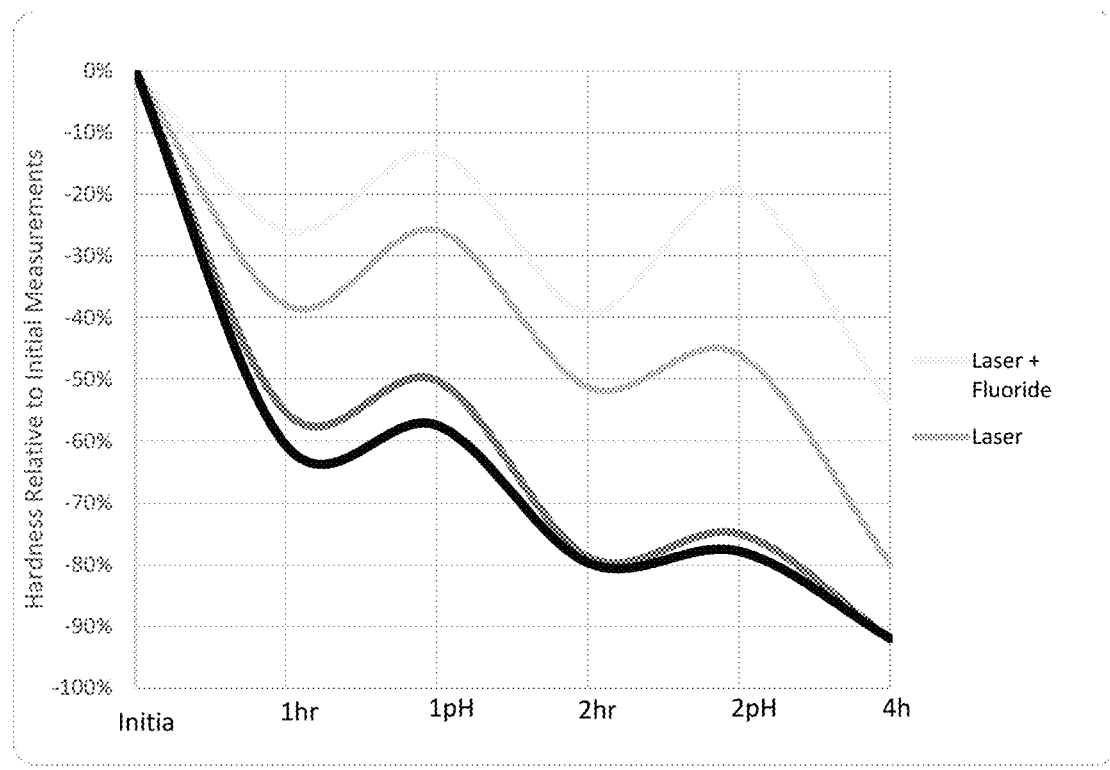
FIG. 8B is an example plot depicting changes in hardness of various tissue surfaces subject to different pH cycle tests, according to various embodiments.

After $\Delta Z$ was determined, each sample was turned on its side so that the laser-irradiated areas were facing up. Samples were then polished on this same side until half of the sample had been removed. Occasional loss of sample occurred due to unexpected damage to the surface or mishandling. Using the same indenter, samples were indented 10 times on the laser-irradiated and non-irradiated control surfaces on each region. The symmetry and quality of each indent was checked under the microscope and the lengths of the indents were measured. Surface loss was then measured at the edge of the nail polish using the built-in 3D stage on the microscope. It was determined as the change in height from the edge of the masked surface to the top of the adjacent unmasked enamel surface. Measurements were taken along the entire length of the boundary region at least every 50 µm, obtaining at least 10 measurements for each boundary region. The surface loss and hardness measurements were combined as $\Delta S = h2/(h1+h2)*$vol % as depicted in FIG. 7, where vol % is calculated from the indents as described above. FIG. 7 depicts a diagram of creating an indent on enamel (left) and a cross-sectional view of the indent site (right). For the calculation of $\Delta S$, h1=surface loss, h2=microhardness indent height, and vol % is calculated from the size of the indent on the surface. $\Delta S$ is a representation of the amount of mineral loss on the surface relating to a slow surface mineral loss; whereas, $\Delta Z$ is a measure of mineral loss in depth relating to a caries-like formation under the surface. Data were analyzed on a log-scale using Welch's ANOVA and post-hoc Games-Howell tests between groups. FIG. 8A is an example chart showing knoop hardness number measurements of various tissue surfaces subject to different pH cycle tests, according to various embodiments. FIG. 8B is an example plot depicting changes in hardness of various tissue surfaces subject to different pH cycle tests, according to various embodiments.

Figure 9:
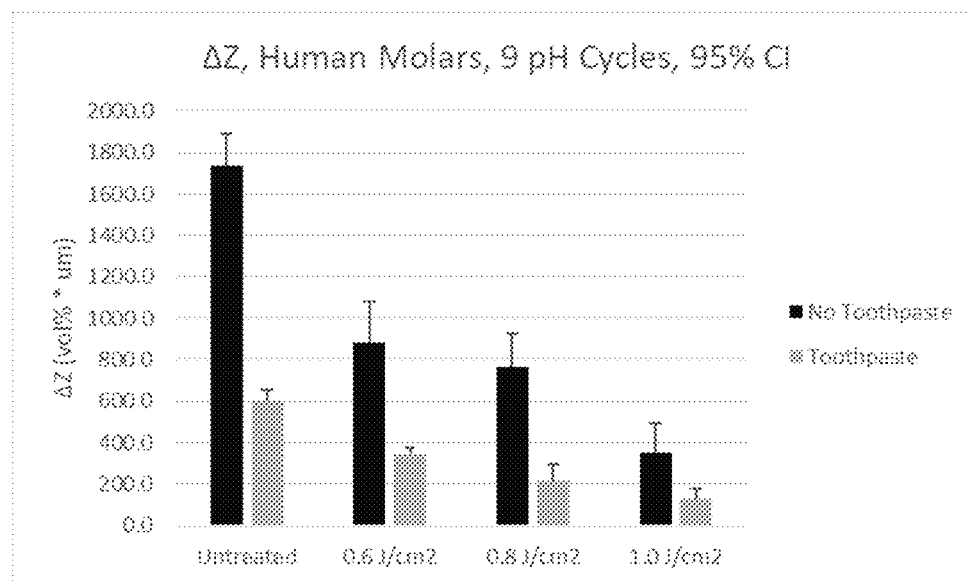
FIG. 9 is an example chart showing $\Delta A$ measurements of various tissue surfaces subject to treatments at different fluence levels, according to various embodiments.

$\Delta Z$ values, shown in Table 1 and FIG. 9, provide a measure of caries-like lesion formation and serve as a metric for comparing treatments with different laser settings. For the range of fluences used, there were no observed superficial structural changes. However, there were occasional signs of minor fracture-like structural changes under the surface for the areas irradiated with 1.0 J/cm², possibly related to subsurface thermal fracturing.

Welch's ANOVA applied to the data showed that there were significant differences between the groups ($F_{11,40}$=81.0, p<0.001). The average reduction in $\Delta Z$ from use of additional fluoride (groups 4-6) without laser-irradiation was ~65% (p<0.001). Reductions in $\Delta Z$ from laser irradiation alone were observed (see groups 1-3 in Table 1), which indicates that an effective remineralization can and does occur, with or without the presence of additional fluoride. Post-hoc Games-Howell tests showed that the combination treatment of laser-irradiation and additional fluoride provided the most significant benefit in reducing $\Delta Z$ for each of the laser fluences used (p<0.01 for all). Although pH-cycling with fluoride toothpaste alone revealed a benefit in caries inhibition, application of fluoride toothpaste in an area that had been irradiated as described herein resulted in the most significant and unexpectedly high reduction in caries formation, with as high as a ~92% (p=0.001) reduction in $\Delta Z$ compared to the untreated control areas.

Figure 10A:
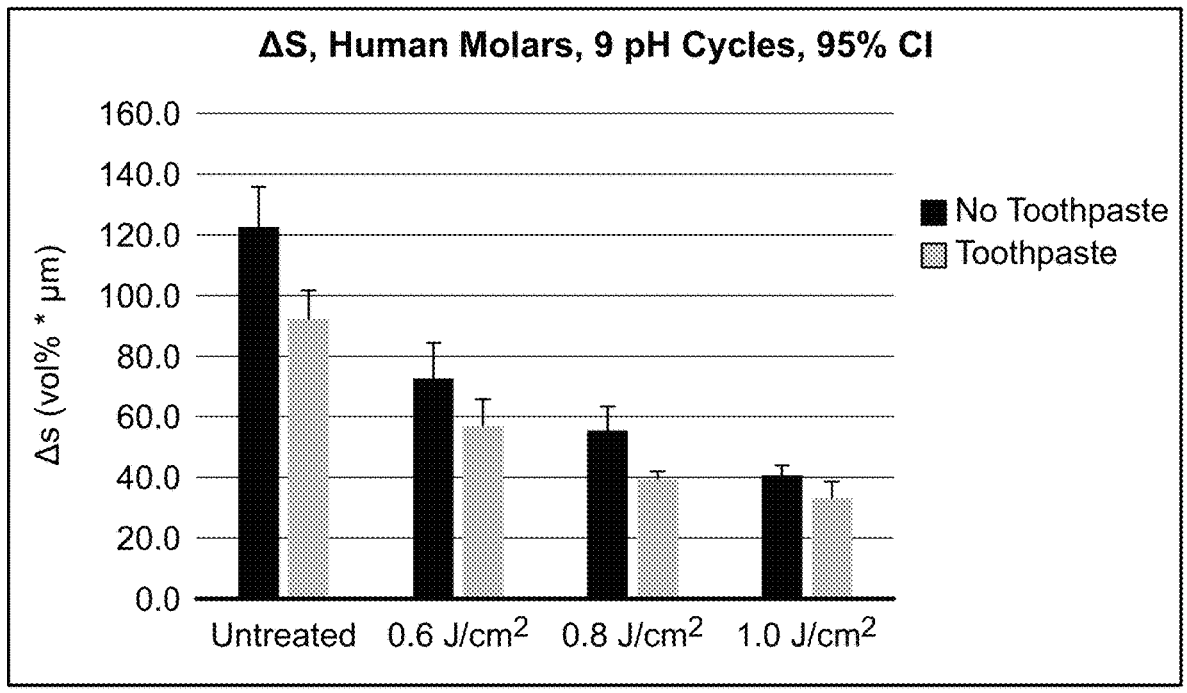
FIGS. 10A-C are an example charts showing $\Delta S$ measurements, surface loss measurements, and surface microhardness measurements, respectively, of various tissue surfaces subject to treatments at different fluence levels, according to various embodiments.
Figure 10B:
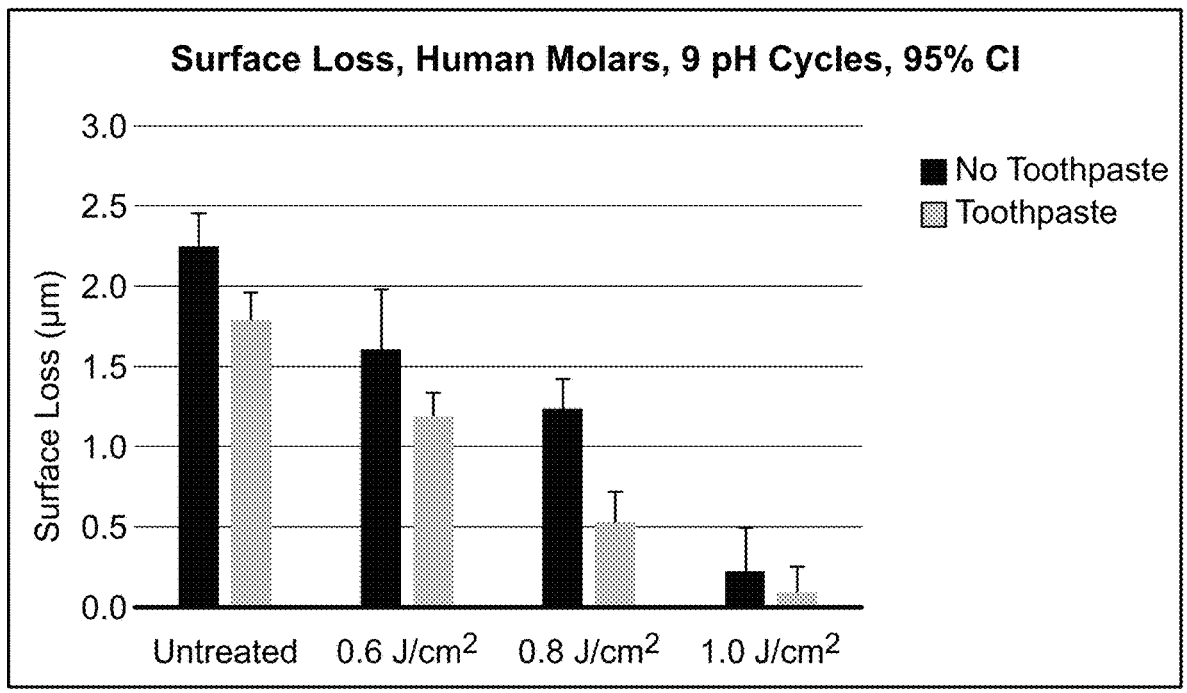
Figure 10C:
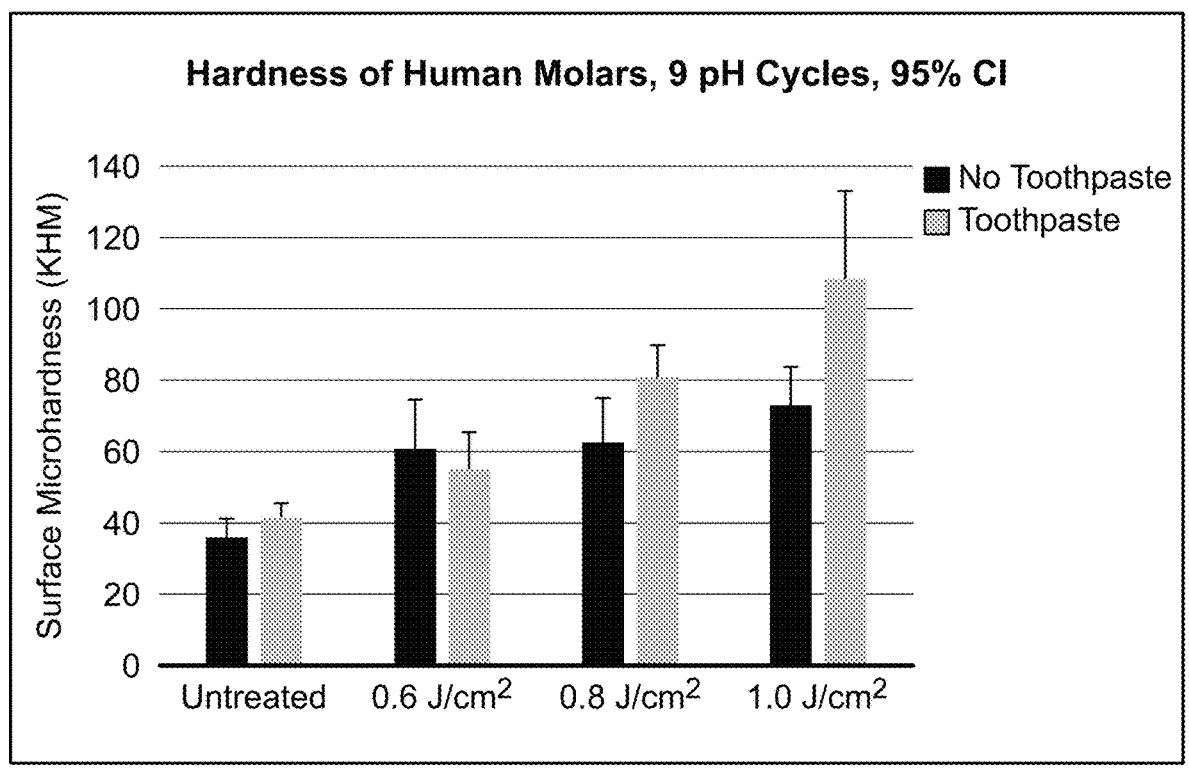

Table 2 and FIGS. 10A-10C show a combination of the surface metrics, in the form of $\Delta S$. As with $\Delta Z$, Welch's ANOVA applied to $\Delta S$ values showed that there were significant differences between groups ($F_{11,36}$=39.5, p<0.001). ANOVA showed no differences within the non-irradiated groups without additional fluoride ($F_{2,12}$=1.16, p>0.05) or with additional fluoride ($F_{2,16}$=0.22, p>0.05). The general trends for $\Delta S$ were similar to those observed for $\Delta Z$ in relation to laser fluence. $\Delta S$ values showed no significance from fluoride use alone relative to untreated controls through post-hoc Games-Howell tests (p>0.05). However, comparing all data without additional fluoride to that with additional fluoride using Student's t-test, a significant reduction of $\Delta S$ by ~18% (p<0.001) was found. $\Delta S$ revealed that laser-irradiation alone at 9.3 µm inhibits surface mineral loss by as much as ~64% (p=0.004). Furthermore, a combination of 1 J/cm² µser-irradiation coupled with fluoride application from toothpaste showed an unexpectedly high reduction in surface mineral loss of ~72% (p<0.001) compared to the untreated control.

Figure 11A:
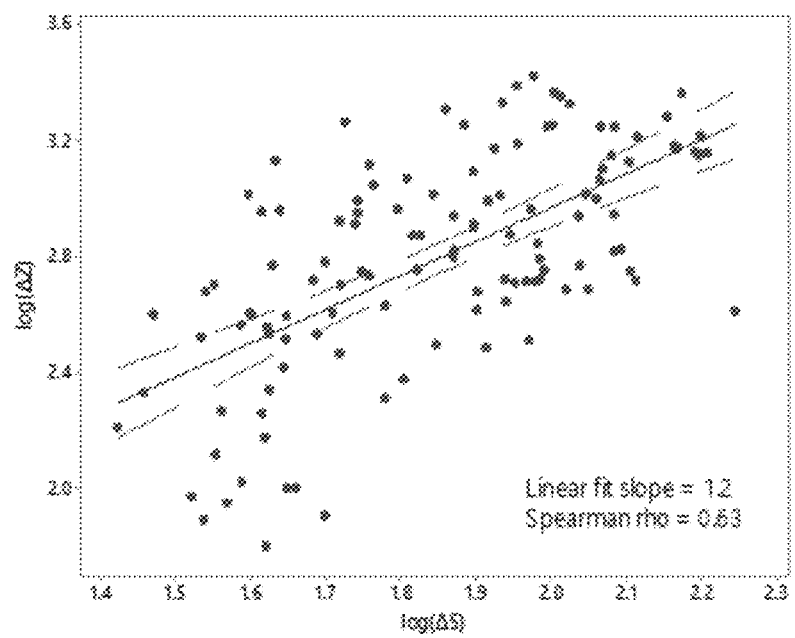
FIGS. 11A-B are graphs showing example $\Delta A$ vs. $\Delta S$ measurements, according to various embodiments.
Figure 11B:
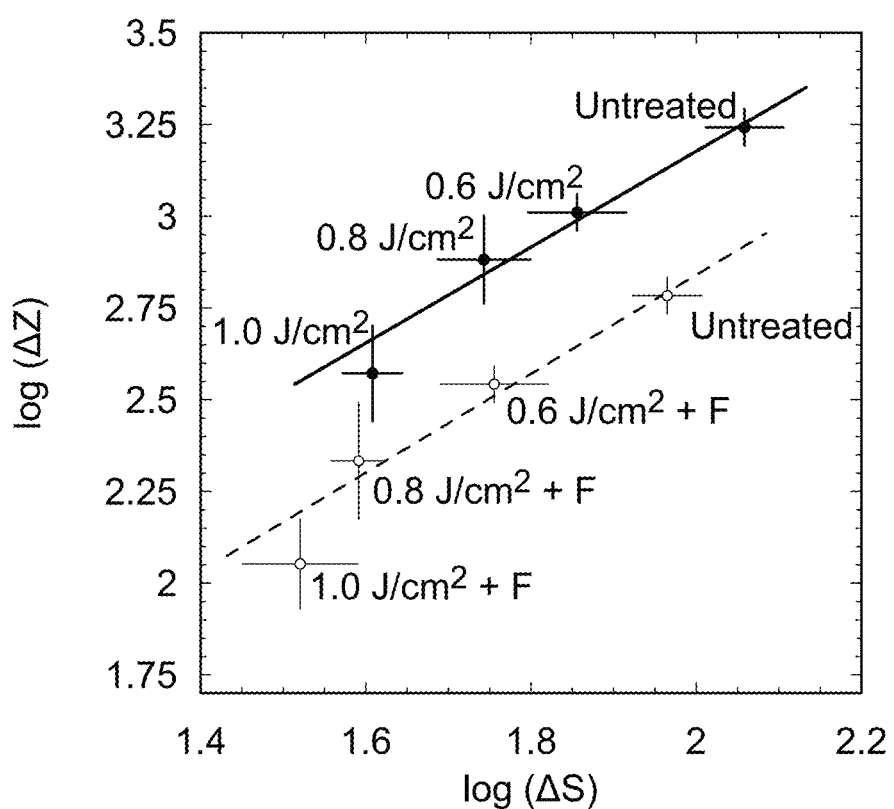

FIG. 11A is a plot of $\Delta Z$ values as a function of $\Delta S$ values for the measurements collected in the above-described experiment. $\Delta Z$ and $\Delta S$ values followed a log-normal distribution, and a linear trend between them was observed with a Spearman rho of 0.63 (p<0.001). FIG. 11B shows linear regression fits (on a log scale) when the data points were averaged according to treatment group. Since the control and toothpaste-cycled sets were different in methodology, they are treated as distinct sets. The linear fits for these two sets have very similar slopes, ~1.3, both with an $R^2$>0.95. This discovery provides two very important pieces of information. One is that the overall effect of fluoride on caries and acid resistance can be quantified by the vertical shift in the curve, revealing that fluoride provides a 50-60% inhibition in caries formation/acid penetration. The other is that the benefit of the laser can be quantified for each pulse fluence.

Averaged both with and without additional fluoride, ΔZ and ΔS were remarkably improved by ~39%, 59%, and 72% after laser-irradiation of 0.6, 0.8 and 1.0 J/cm², respectively, compared to areas without laser-irradiation.

FIG. 12A provides example data, including ΔZ and ΔS measurements, for tissues lased at various fluences and with and without the application of fluoride. FIG. 12B is a graph of measured ΔZ values for various fluences for treatments combined with fluoride and without fluoride, as well as an indication of an example effective treatment zone. FIG. 12C is a graph of measured ΔS values for various fluences for treatments combined with fluoride and without fluoride, as well as an indication of an example effective treatment zone.

In various embodiments, laser irradiation at 9.3 μm creates an acid-resistant form of hydroxyapatite that occurs at temperatures in which a large amount of the carbonate groups in the carbonated-hydroxyapatite mineral of the dental enamel are removed. This can allow a crystallization of fluoride-containing hydroxyapatite in these weak areas to occur, thereby reducing the penetration of acid under the resistant layer. Other organic components, which largely exist as a glue-like network holding adjacent rods together, may also be removed near the surface during irradiation. This surface change has been described previously as a "glazing" of the surface.

In various embodiments, the benefit of laser-irradiation under the laser conditions tested, even without the use of fluoride, is significant. The softening of the surface and formation of an underlying lesion can be slowed significantly. This may be an indication that a crystallization of the "weakened" sites occurs from dissolved minerals (primarily calcium and phosphate), despite an initial acid exposure. Due to this remineralization effect, the benefit of laser-induced acid resistance can, outweigh the risks associated with structural changes to the surface. In some embodiments, the introduction of fluoride in the cycling process can enhance the acid resistant properties of the layer, which may be due at least in part to the inherent resistance of fluorapatite to dissolution. The laser treated area may encourage an uptake of fluoride by the surface, together with calcium and phosphate, resulting in the observed beneficial effect of the pair of treatments in combination. As described below, in some embodiments that application of fluoride can be performed with delivery of the coolant with the laser treatment system 100. However, the invention also contemplates delivery of fluoride from other sources, e.g., separate from delivery through the laser treatment system 100, either as part of a dental office visit or elsewhere (e.g., brushing teeth or using mouthwash at home).

The inventions described herein demonstrate a direct correlation between the surface mineral loss (ΔS) and the size of a carious lesion (ΔZ). In some embodiments, one explanation for this is that a complete remineralization back to the original density may not be possible, as the crystallization is random and may introduce insufficiently packed crystals. Through laser irradiation of the surface, the softening of the enamel from acid exposure may be significantly reduced, which was evident in both measures of surface (erosion) or depth (caries) mineral loss. The resistance to acid may be further enhanced by use of a high-concentration fluoride application, such as prescription mouthwash or varnish, which would also help to quickly remineralize any weak sites with fluorapatite, possibly even before a patient leaves the treatment clinic, as the laser-irradiated area is capable of increasing the rate of fluoride uptake. In this work, erosion and caries resistance may be enhanced by around 50-60% using fluoride-containing toothpaste and can be increased by a further 40-80% using a laser treatment with a 9.3 μm $CO_2$ laser.

As used herein, the term "working range" means the distance along the length of the laser beam at which the laser beam has a fluence capable of treating the tissue (e.g., removing carbonate). Conventional devices have a relatively short working range, typically focused tightly around a focal point of the laser beam based on a desire to not waste any energy along the length of the laser. The laser treatment system of the present invention can, in some embodiments, tolerate a longer working range, so as to enable an operator to move their hand (and, correspondingly, the laser beam), while still treating the treatment area effectively. In other words, in certain embodiments, the amount of energy delivered to the target tissue does not change over a relatively long distance along the axis between the exit orifice 8 and the hard tissue (e.g., more than 0.5 cm, more than 1 cm, more than 1.5 cm, more than 2 cm, more than 3 cm, more than 4 cm, etc.) to accommodate for hand movements, variability in the user's holding of the handpiece standoff and other human factors. The concept of a working range is described in more detail with reference to the phrase "depth of treatment" (which can be interchanged with "working range") in U.S. Patent Publication No. 2016/0143703, which is incorporated by reference herein in its entirety and attached as Appendix C.

In some embodiments, the hand piece 1 can also be adapted to transmit fluids to the treatment region, e.g., cooling fluids and/or fluoride-based fluids. The fluids can be transported using any known technique, e.g., through fluid tubing 5 that run along the handpiece 1 and bypass the optical cartridge 2. The cooling fluids can be useful to minimize and avoid excessive heating of the tissue. As discussed above, the fluoride based fluids may result in improved and more effective treatment. In some cases, both cooling and fluoride based fluids can be delivered through the same tubings 5. In other cases, the hand piece 1 can include separate tubing for each of the cooling fluid and fluoride-based fluid. Other desirable fluids may also be transported through the hand piece 1.

In certain embodiments, the laser beam is accompanied with a marking beam (e.g., green in color) that serves as guidance of the location of the laser beam on the target tissue. In some instances, the irradiation of the laser may occur in a pattern. A visual or sonar feedback can optionally be integrated within the system 100 to indicate to the user the need to move to a new target area. A visual feedback indicating a new target area can include a stationary guidance beam (e.g., a green point projected on the tissue). For example, while the tissue is being exposed to the laser, a pattern can be displayed on the tissue. When enough energy has been delivered, the laser can stop scanning and a point object can being projected on the target tissue. Alternatively, a sonar feedback can be provided to indicate a pattern and/or amount of energy delivery.

FIG. 13 is a chart including example laser and operation parameters for the laser treatment system 100. The parameters may be designed to have a desired outcome efficiency to remove carbonate without damaging the treatment surface material. In some embodiments, the laser beam may be spatially scanned to provide different pulse energy at different locations, as will be appreciated by those skilled in the art.

Each numerical value presented herein is contemplated to represent a minimum value or a maximum value in a range for a corresponding parameter. Accordingly, when added to the claims, the numerical value provides express support for claiming the range, which may lie above or below the numerical value, in accordance with the teachings herein. Every value between the minimum value and the maximum value within each numerical range presented herein (including the low, nominal, and high values shown in the chart shown in FIG. 13), is contemplated and expressly supported herein, subject to the number of significant digits expressed in each particular range.

Having described herein illustrative embodiments of the present invention, persons of ordinary skill in the art will appreciate various other features and advantages of the invention apart from those specifically described above. It should therefore be understood that the foregoing is only illustrative of the principles of the invention, and that various modifications and additions, as well as all combinations and permutations of the various elements and components recited herein, can be made by those skilled in the art without departing from the spirit and scope of the invention. Accordingly, the appended claims shall not be limited by the particular features that have been shown and described but shall be construed also to cover any obvious modifications and equivalents thereof.

What is claimed is:

1. A method for treating a hard dental tissue, the method comprising the steps of:
   generating a laser beam using a laser source;
   directing the laser beam to a treatment surface of the hard dental tissue using an optic in optical communication with the laser source; and
   controlling the laser source and the optic using a controller to deliver the laser beam to the treatment surface to treat an area of the hard dental tissue at a rate in a range from 10 $cm^2$/min to 20 $cm^2$/min with a fluence in a range from 0.4 $J/cm^2$ up to 1.2 $J/cm^2$ to:
      remove at least some carbonate from the treatment surface to generate an acid resistant surface without damaging the hard dental tissue;
      thereafter determining a depth mineral loss value of the hard dental tissue; and
      confirming the depth mineral loss value of the hard dental tissue is at least 10% relative to untreated hard dental tissue.

2. The method of claim 1, wherein the laser source comprises a $CO_2$ laser source.

3. The method of claim 2, wherein the laser beam comprises a wavelength in a range from 9 μm to 11 μm.

4. The method of claim 1, wherein the optic comprises at least one of a galvanometer and a turning mirror.

5. The method of claim 1, wherein the controller is further adapted to control the laser source to deliver the laser beam to the treatment surface in a series of pulses.

6. The method of claim 5, wherein each pulse in the series of pulses comprises a pulse energy in a range from 0.1 mJ to 50 mJ.

7. The method of claim 5, wherein each pulse in the series of pulses comprises a pulse duration in a range from 1 μsec to 100 μsec.

8. The method of claim 5, wherein the series of pulses comprises a repetition rate in a range from 0.05 Hz to 10 Hz.

9. The method of claim 5, wherein the series of pulses comprises a duty cycle in arrange from 0.1 to 10.

10. The method of claim 5, wherein the controller is adapted to deliver the series of pulses to the treatment surface in a pattern.

11. The method of claim 10, wherein the pattern comprises a diameter in a range from 1 mm to 5 mm.

12. The method of claim 10, wherein the pattern comprises a number of locations in a range from 1 to 1,000.

13. The method of claim 12, wherein the pattern comprises 217 locations.

14. The method of claim 12, wherein a spacing between each location in the pattern is in a range from 0.1 mm to 0.5 mm.

15. The method of claim 1, wherein the controlling step further comprises using the controller to control the laser source to deliver the laser beam to the treatment surface to, when combined with a fluoride treatment, reduce a depth mineral loss value of the dental tissue by at least 20% relative to hard dental tissue subject to the fluoride treatment.

16. The method of claim 15, further comprising the step of delivering the fluoride treatment to the treatment surface.

17. The method of claim 1, wherein the controlling step further comprises using the controller to control the laser source to deliver the laser beam to the treatment surface to reduce a surface mineral loss value of the dental tissue by at least 68% relative to untreated dental tissue.

18. The method of claim 1, wherein the controlling step further comprises using the controller to control the laser source to deliver the laser beam to the treatment surface to, when combined with a fluoride treatment, reduce a surface mineral loss value of the dental tissue by at least 18% relative to hard dental tissue subject to the fluoride treatment.

* * * * *

UNITED STATES PATENT AND TRADEMARK OFFICE
CERTIFICATE OF CORRECTION

PATENT NO. : 12,233,278 B2
APPLICATION NO. : 18/413943
DATED : February 25, 2025
INVENTOR(S) : Charles Kerbage et al.

Page 1 of 1

It is certified that error appears in the above-identified patent and that said Letters Patent is hereby corrected as shown below:

In the Claims

In Column 14, Claim 9, Line 14, delete "in arrange" and insert --in a range--.

Signed and Sealed this
Third Day of February, 2026

John A. Squires
*Director of the United States Patent and Trademark Office*